(12) United States Patent
Furlan et al.

(10) Patent No.: US 7,906,767 B2
(45) Date of Patent: Mar. 15, 2011

(54) EXCITATION AND IMAGING OPTICS FOR FLUORESCENCE DETECTION

(75) Inventors: Alan Furlan, Immensee (CH); Joachim Wietzorrek, Zug (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 62 days.

(21) Appl. No.: 12/506,792

(22) Filed: Jul. 21, 2009

(65) Prior Publication Data

US 2010/0019157 A1    Jan. 28, 2010

(30) Foreign Application Priority Data

Jul. 25, 2008  (EP) .................................... 08013392

(51) Int. Cl.
*G01J 1/58* (2006.01)
(52) U.S. Cl. ................. 250/459.1; 250/363.01
(58) Field of Classification Search ............. 250/363.01, 250/458.1, 459.1, 461.1, 461.2; 435/288.7
See application file for complete search history.

(56) References Cited

U.S. PATENT DOCUMENTS

| | | |
|---|---|---|
| 6,246,525 B1 | 6/2001 | Ikami |
| 6,498,690 B2 | 12/2002 | Ramm et al. |
| 6,686,582 B1 | 2/2004 | Voelcker et al. |
| 7,102,131 B2 | 9/2006 | Spolaczyk et al. |
| 7,301,637 B2 | 11/2007 | Lossau et al. |
| 7,387,891 B2* | 6/2008 | Boege et al. ............... 435/288.7 |
| 2002/0005493 A1 | 1/2002 | Reese et al. |
| 2002/0159057 A1 | 10/2002 | Odoy et al. |
| 2002/0192808 A1* | 12/2002 | Gambini et al. ........... 435/287.2 |
| 2003/0011772 A1 | 1/2003 | Abe et al. |
| 2005/0064427 A1 | 3/2005 | Gluch et al. |
| 2006/0166355 A1* | 7/2006 | Gutekunst ................ 435/288.7 |
| 2006/0291048 A1 | 12/2006 | Olszak et al. |

FOREIGN PATENT DOCUMENTS

| | | |
|---|---|---|
| DE | 19919092 A1 | 11/2000 |
| DE | 10017824 A1 | 11/2001 |
| DE | 10017824 B4 | 3/2004 |
| EP | 0987540 A2 | 3/2000 |
| EP | 0987540 A3 | 7/2000 |
| EP | 1275954 A2 | 1/2003 |
| EP | 1275954 A3 | 1/2004 |
| EP | 1406082 A1 | 4/2004 |
| EP | 1681555 A1 | 7/2006 |
| EP | 1681556 A1 | 7/2006 |
| EP | 1681555 B1 | 3/2007 |
| EP | 1681556 B1 | 4/2007 |
| EP | 0987540 B1 | 8/2008 |
| JP | 2002014044 A | 1/2002 |
| WO | 9960381 A1 | 11/1999 |
| WO | 03069391 A1 | 8/2003 |
| WO | 03098279 A2 | 11/2003 |
| WO | 03098279 A3 | 11/2003 |
| WO | 2004074820 A2 | 9/2004 |
| WO | 2004074820 A3 | 9/2004 |

* cited by examiner (Continued)

*Primary Examiner* — David P Porta
*Assistant Examiner* — Marcus H Taningco
(74) *Attorney, Agent, or Firm* — Vivien Banholzer

(57) ABSTRACT

The invention concerns an optical instrument for imaging fluorescence signals from an arrangement of a plurality of individual detection sites, for example the wells of a microtitre plate. In order to improve the light yield of the fluorescence excitation with excitation light as well as the light yield of the detection of the fluorescence signals, an objective array is provided which is arranged in the beam path between the field lens and the detection sites and comprises a field lens array with field lens array elements and a pupil lens array with pupil lens array elements. In order to improve the channel separation and suppress interfering light the objective array can comprise a diaphragm array with in each case two diaphragm openings per detection site.

15 Claims, 12 Drawing Sheets

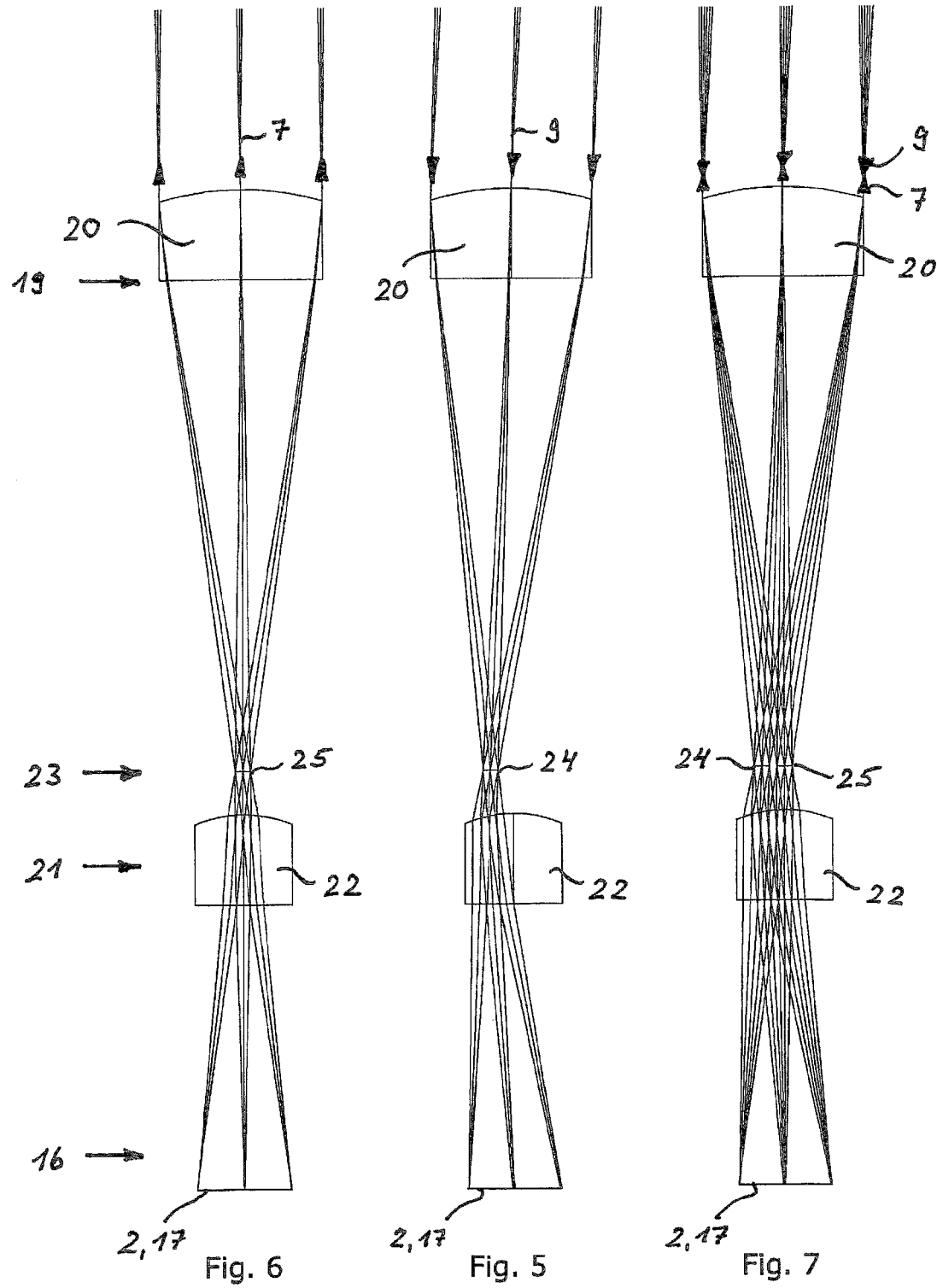

EXCITATION AND IMAGING OPTICS FOR FLUORESCENCE DETECTION

CROSS-REFERENCE TO RELATED APPLICATION

The present application claims the benefit of EP Appl. No. 08013392.9 filed Jul. 25, 2008, the content of which is hereby incorporated herein by reference in its entirety.

FIELD OF THE INVENTION

The present invention relates to the field of DNA analysis. In particular the present invention relates to a device for the parallel imaging of fluorescence intensities of a plurality of detection sites and in this connection in particular the excitation and imaging optics for the fluorescence detection of fluorescence signals.

DESCRIPTION OF PRIOR ART

In electrophoretic methods, proteins or DNA may be labelled with a fluorescent probe in order to visualize their electrophoretic bands in gels or columns. Furthermore, most of the previous applications of biochips are based on a fluorescence reading in which the specific binding of a fluorescently labelled target molecule to a probe molecule which is immobilized on a solid support is monitored. Applications in DNA analysis in the liquid phase include fluorescent hybridization probes such as the dye SyBRGreen 1® which binds to double-stranded DNA or FRET probes (fluorescence resonance energy transfer) which utilize two fluorescent probes and energy transfer. A very important application for fluorescence methods in the liquid phase is the determination of the quantity of PCR products in real time called "real time PCR".

The PCR (Polymerase Chain Reaction) is a method for amplifying double-stranded DNA (deoxyribonucleic acid). In a PCR apparatus a block for thermal cycling has one or more holding devices with sample vessels (wells) containing a mixture of components for a reaction which, starting with an initial amount of DNA, are used to obtain more DNA. The starting components comprise a "seeding amount" of DNA in an aqueous solution, certain primary DNA, DNA elements, enzymes and other chemicals. The temperature of the block is cycled between a low extension phase of the PCR reaction of about 60° C. during which all DNA strands are recombined into double strands, and a higher denaturing phase of about 95° C. during which the DNA is denatured or separated into single strands. Such a temperature program essentially doubles the DNA in each cycle which enables replication of substantial amounts of DNA from small initial amounts. The quantitative determination of the DNA is carried out using fluorescence measurements, also in real time.

In all these cases an optical instrument, i.e. an excitation and reading device for fluorescence, is required for providing light at a certain wavelength in to excite the fluorescent marker used in the assay and for detecting the fluorescence light from the marker emitted at a somewhat different wavelength. A major problem in fluorescence measuring devices is the enormous intensity of the excitation light in comparison to the fluorescence light which is emitted by the fluorescent marker and one therefore has to ensure that the excitation beam does not strike the detector in order to be able to exactly monitor the fluorescence signals. In other words, the beam path (light path) of the excitation light must at least partially differ from the beam path (light path) of the fluorescent light. The following measures are commonly taken for this purpose:

a) a spectral separation is done by excitation and emission filters (the spectra of which do not significantly overlap).
b) the use of a vertical illumination (or also epi-illumination) or of a side illumination.

In both cases a) and b) the illumination light beams do not point in a direction that can be directly detected (dark field). One requires at least one reflection, elastic scattering or fluorescence (inelastic scattering). Measure b) is usually used as a support for measure a) because the filter blocking according to measure a) is not perfect.

Implementing the principle of fluorescence is relatively simple if only one fluorescent probe in the liquid phase of e.g. a capillary has to be monitored. In this case a source of white light together with a set of dichroic mirrors and filters is for example sufficient to fulfill the requirements. However, when more than one fluorescent marker are present in the sample, it is necessary to monitor a lateral distribution of the positions on a solid support or the fluorescence of a microtitre plate (except when different dyes are present and detected in a single sample vessel) and the requirements of the optical instrument for the fluorescence measurement are more difficult to fulfill.

Basically there are two different strategies for exciting and monitoring the fluorescence of a lateral distribution of detection sites. The first strategy is to scan the lateral distribution of detection sites in which the individual detection sites are each individually analysed in succession. The second strategy is to simultaneously illuminate the entire distribution of detection sites and to image the corresponding fluorescence on a plurality of optical sensors e.g. a CCD chip. The scanning strategy has the obvious disadvantage that either the carrier has to be moved in two dimensions (see e.g. WO 03/069391, DE 102 00 499), or the detector has to be moved relative to the carrier (US 2002/159057), or the detector has to be moved in one dimension and the carrier has to be moved in the other dimension or the optical system must have a one-dimensional or two-dimensional scanning means i.e. galvo mirrors. On the other hand, the main difficulty of the second strategy of illuminating the entire carrier simultaneously is to ensure a uniform illumination over the entire distribution of detection sites.

An alternative to the uniform illumination over the entire distribution of detection sites is to utilize an arrangement of light sources wherein each detection site is illuminated by its own light source. DE 101 31 687 describes a strategy for evaluating PCR in a thermocycler with a plurality of wells using a beam splitter and an arrangement of LEDs for illumination. DE 101 55 142 describes a dark field monitoring of fluorescence signals where the microarray is also illuminated by an arrangement of LEDs but no beam splitter is required in this embodiment.

With regard to the requirement of at least partially separating the beam path of the excitation beam and of the fluorescent light (of the detected fluorescence signals), there are again at least two different alternatives. The first alternative is the so-called "epi-illumination" in which beam splitters are used and the excitation beam and the fluorescence light share at least a part of the optical system. The second alternative is to use inclined illumination. In this case the excitation beam is arranged in such a manner that it has a certain angle to the normal of the carrier surface and the corresponding reflection of the excitation beam is outside of the angle of aperture of the detection system (e.g. US 2002/0005493 A1, EP 1 275 954 A2).

US 2003/0011772 A1 describes an optical device for simultaneously observing a plurality of fluorescent dyes in a probe using a beam splitter. DE 197 48 211 A1 discloses a system for simultaneously monitoring the fluorescence signals which are generated in the wells of a microtitre plate using a beam splitter, a field lens and an arrangement of lenses which focus the light onto each well. The detection is carried out by forming an image of the light on an arrangement of photodiodes or on a CCD chip. The fluorescence light which is collected in this embodiment of the system is determined by the amount of dyes which are excited by the light cone of the focussing lens and therefore depends on the fill level of the well.

WO 99/60381 describes a device for simultaneously monitoring PCR reactions in a plurality of wells in a block whose temperature is controlled in cycles. The optical components of this device again comprise a beam splitter, a field lens, an arrangement of lenses for the wells which focus the individual light beams into each well, and a detection means which focuses the emitted light onto for example a CCD detector. Since an arrangement of lenses for the wells is required, the size and lateral density of the individual detection sites is limited. The light yield of this arrangement is low and there is considerable crosstalk between the individual detected wells i.e. the channel separation is low.

JP 2002014044 describes a fluorometric device for monitoring fluorescence which is generated in a plurality of wells. The optical components comprise a beam splitter and a lens system for commonly illuminating the wells with light which is parallel to the depth direction of the wells. The imaging optical system, however, condenses the light onto a detection means. U.S. Pat. No. 6,498,690 B1 discloses a method for imaging assays with an objective which has a telecentric lens. U.S. Pat. No. 6,246,525 B1 describes an imaging device for imaging a sample carrier with a Fresnel lens. EP 0 987 540 A discloses an imaging device for fluorescent assays which has an imaging unit which comprises a set of telecentric lenses. EP 1 406 082 A describes a fluorescence reading device with telecentric illumination.

EP 1 681 555 B1 describes an improved device for simultaneously monitoring fluorescence signals from a lateral distribution of detection sites where the beam path is optimized with regard to a uniform illumination and exact detection. It comprises an imaging lens arrangement which is arranged such that it transfers the fluorescence signals from the field lens to an optical sensor and has the characteristic feature that the beam path of the excitation light and the beam path of the fluorescence signals from the plurality of individual detection sites are telecentric on the object side of the field lens.

EP 1 681 556 B1 describes a similar, further improved device in which the field lens is arranged such that it generates excitation light with an angle of incidence to the flat support of the arrangement of a plurality of individual detection sites which is larger than 0°.

Although good results can be obtained with these prior art devices, the light yield can be further improved in order to enable even smaller fluorescence signals to be detected or to allow detection of fluorescent signals with an improved signal-to-noise ratio or with an improved resolution.

SUMMARY OF THE INVENTION

In a first aspect, the invention relates to an optical instrument for imaging fluorescence signals from an arrangement of a plurality of individual detection sites comprising:
a holding device for holding a planar support with an arrangement of a plurality of individual detection sites;
at least one light source for emitting light comprising at least one excitation frequency;
an optical sensor for receiving fluorescence signals from the arrangement of a plurality of individual detection sites and capable of generating computer-readable primary data;
a field lens for transferring the excitation light from the light source to the arrangement of a plurality of individual detection sites and transferring fluorescence signals from the arrangement of a plurality of individual detection sites to the optical sensor;
an excitation lens arrangement for transferring excitation light from the light source to the field lens; and
and imaging lens arrangement for transferring fluorescence signals from the field lens to the optical sensor;
wherein:
the optical instrument comprises an objective array comprising a field lens array having field lens array elements and a pupil lens array comprising pupil lens array elements, wherein the objective array is located in the light beam path between the field lens and the arrangement of a plurality of individual detection sites,
and wherein:
a diaphragm array forms a mask for the illumination pupils from the excitation light and the detection pupils from the fluorescence signals, wherein the diaphragm array has diaphragm array elements, each of said diaphragm array element comprising one or more diaphragm openings and each of said diaphragm array element being allocated one field lens array element and one pupil lens array element and forming a mask for the beam path through the respective field lens array element and pupil lens array element.

In a second aspect, the invention relates to an optical instrument for imaging chemiluminescence or bioluminescence signals from an arrangement of a plurality of individual detection sites comprising:
a holding device for holding a planar support with an arrangement of a plurality of individual detection sites;
an optical sensor for receiving chemiluminescence or bioluminescence signals from the arrangement of a plurality of individual detection sites and capable of generating computer-readable primary data;
a field lens for transferring chemiluminescence or bioluminescence signals from the arrangement of a plurality of individual detection sites to the optical sensor;
an imaging lens arrangement for transferring chemiluminescence or bioluminescence signals from the field lens to the optical sensor;
wherein the optical instrument has an objective array comprising
a field lens array with field lens array elements and a pupil lens array with pupil lens array elements, and
wherein the objective array is arranged in the light beam path between the field lens and the arrangement of a plurality of individual detection sites.

In a third aspect, the invention relates to a real-time PCR instrument comprising:
an optical instrument according to the invention as defined herein,
means for heating and cooling a support with one or more wells each containing a reaction mixture capable of performing a PCR reaction.

In a fourth aspect, the invention relates to an analytical system for simultaneously performing and monitoring a plurality of PCR reactions in real-time comprising:
- a multiwell plate as an arrangement of a plurality of individual detection sites each containing a reaction mixture capable of performing a PCR reaction,
- fluorescent DNA binding entities capable of generating fluorescence signals and
- a real-time PCR instrument according to the invention as defined herein comprising an optical instrument according to the invention as defined herein for illuminating the plurality of individual detection sites of the multiwell plate with light and for detecting the fluorescence signals from each well of the multiwell plate by an optical sensor capable of receiving the corresponding fluorescence signals in order to generate computer-readable primary data.

In a fifth aspect, the invention relates to a method for amplifying, detecting and/or quantifying a plurality of DNA target sequences comprising:
- providing a composition or a reaction mixture which is able to carry out PCR reactions;
- treating the reaction mixture according to a thermocycling protocol such that an amplification of the plurality of DNA target sequences can take place; and
- determining the presence and the number of each DNA sequence at least once after a plurality of amplification cycles using fluorescent DNA binding entities and a real-time PCR instrument according to the invention as defined herein.

BRIEF DESCRIPTION OF THE FIGURES

FIG. 5 shows a section through a channel of an objective array according to the invention with the beam path for fluorescence excitation.

FIG. 6 shows a section through a channel of an objective array according to the invention with the beam path for fluorescence detection.

FIG. 7 shows a section through a channel of an objective array according to the invention with a diaphragm with two separate diaphragm openings for fluorescence excitation and fluorescence detection.

DETAILED DESCRIPTION OF THE INVENTION

Figure 1A:
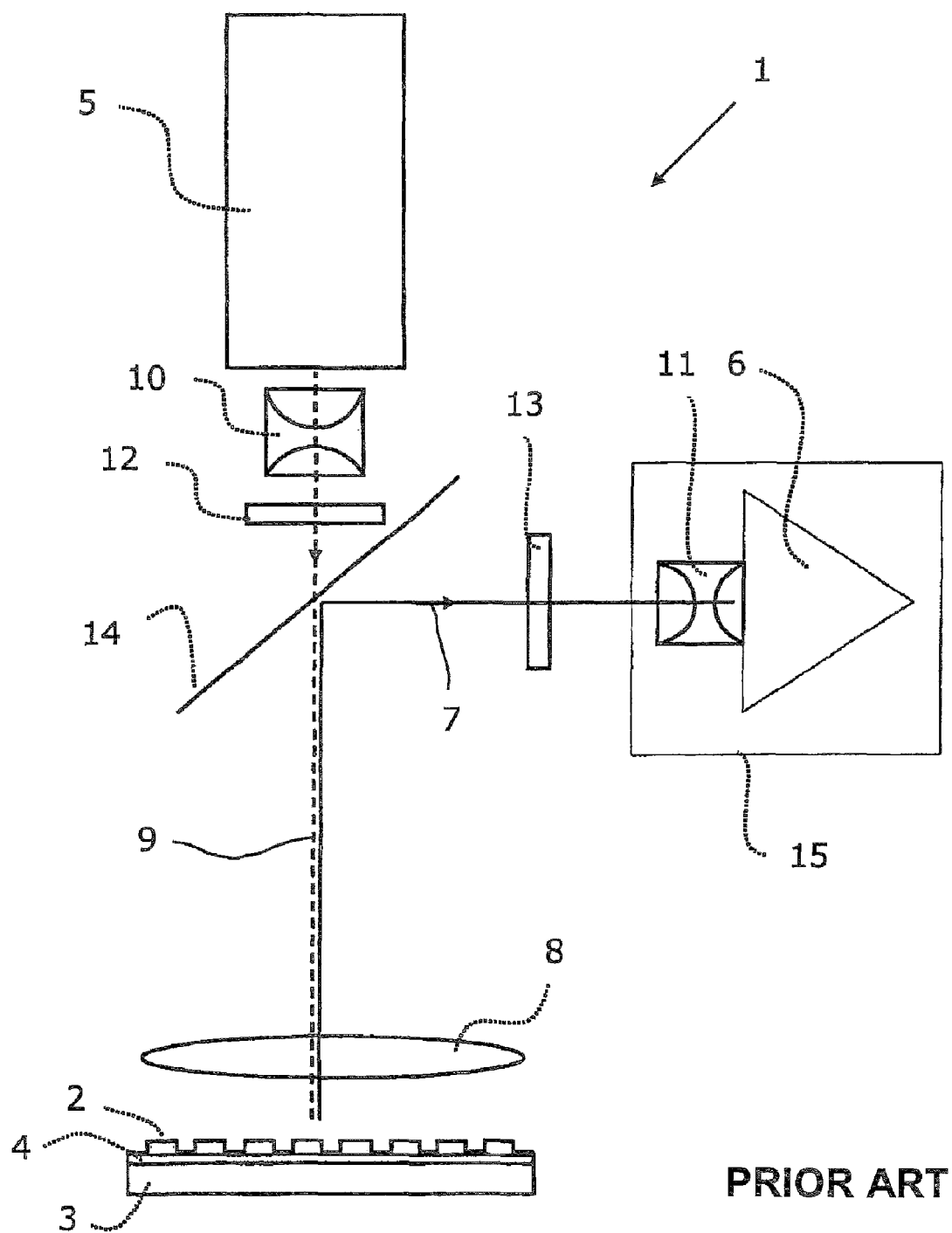
FIG. 1a shows a schematic diagram of an embodiment of the optical instrument according to the prior art.

As mentioned hereinabove, the object of the present invention is to provide an improved device or an improved optical instrument for simultaneously monitoring fluorescence signals from a lateral distribution of a plurality of individual detection sites by optimizing the beam path with regard to a higher light yield. In one aspect of the present invention the problem to be solved relates to improvements in the monitoring of real-time multiplex PCR in a microtitre plate format.

Hence the invention is directed to an optical instrument for imaging fluorescence signals of an arrangement of a plurality of individual detection sites with a uniform excitation over the entire area of the arrangement, accurate imaging of the corresponding fluorescence signals and a high light yield.

This object is achieved according to the invention by an optical instrument having the features of patent claim 1. Various embodiments result from the dependent and independent patent claims and the subsequent description with the attached drawings.

In a certain embodiment the beam path of the excitation light and the beam path of the fluorescence signals from the plurality of individual detection sites are telecentric on the object side of the field lens i.e. the optical instrument uses a telecentric pupil position. More precisely, the beam path on the object side of the field lens and on the object side of the field lens array is telecentric within the scope of the invention. On the other side i.e. between the pupil lens array and the arrangement of a plurality of individual detection sites, the beam path is no longer telecentric. A telecentrism is no longer required here. Each detection site "sees" through the periodic objective array the same non-telecentric pupil for illumination and detection.

The invention not only enables a higher light yield in order to be able to detect even smaller fluorescence signals or to detect fluorescence signals with an improved signal-to-noise ratio or in a better resolution, but also has numerous other advantages e.g. even a more rapid fluorescence measurement. Furthermore, according to the prior art high performance lamps with a high illumination density are used e.g. Xenon arc lamps in order to compensate for the previously low light yield. However, such high performance lamps do not only have a high thermal dissipation loss which requires an elaborate heat removal or cooling mechanism but also have a relatively short lifetime which is usually of the order of about 500 hours. Accordingly frequent lamp replacement is required in the prior art. If the lamp fails during an ongoing measurement e.g. a real-time PCR, the entire measurement of a certain sample may be lost. The signal gain and the sensitivity improvement by the invention avoids these problems and also creates the possibility of using weaker and thus more long-lasting lamps and also alternative light sources e.g. LEDs with a longer lifetime and higher reliability. Hence, an important advantage of the invention is the elongation of the lifetime of the light source that is used. Thus, in a certain embodiment, the optical instrument of the present invention comprises a LED or a laser, more particularly a LED as a light source.

In the context of this invention an arrangement of a plurality of individual detection sites summarizes objects that are composed of two or more spatially separated and laterally distributed detection sites. The detection sites may for example be wells of a microtitre plate or functionalized surface areas of a microscope slide or glass slide.

Within the scope of this invention the planar support of the arrangement is for example a planar solid phase. In the case of a microarray, the planar support of the arrangement is the surface of this planar solid phase where the detection sites are arranged. In the case of a microtitre plate the planar support of the arrangement is the plane where the openings of the wells are arranged. The flat support of the arrangement is fastened by a holding device in order to immobilize each individual detection site at the target position within the beam path.

Within the scope of this invention the term "light source" encompasses illuminants which emit light with a single frequency or with a plurality of different frequencies. In addition the light source may be an arrangement of more than one of the said illuminants.

In the context of this invention an "optical sensor" (detector, transducer) is a device for converting visible light into electrical signals that can be processed by a computer. The optical sensor can comprise one individual or more optical sensors. A certain embodiment is an optical sensor comprising several optical sensors which are placed in a spatially distributed arrangement which is for example designed to correspond to the arrangement of the plurality of individual detection sites. Certain embodiments include semi-conductor components for example photodiodes or in particular charge-coupled components for example a CCD chip.

Within the scope of this invention a "telecentric optical system" is an optical system with an aperture diaphragm which is projected into infinity by the optical elements between the aperture diaphragm and the object. In other words the main beams of a telecentric optical system are quasi-parallel in the object space. The term "main beams" is used for all light beams which go through the centre of the aperture diaphragm. The terms "object", "object plane" and "object space" are used to describe the planar support with the arrangement of a plurality of individual detection sites. In the telecentric optical system the excitation lens arrangement and the imaging lens arrangement both have their own aperture diaphragm. The telecentric optical system is telecentric for the excitation and the beam path of the detection of the fluorescence signals on the field lens side of the objective array. Each object point in a plane perpendicular to the optical axis corresponds to a main excitation beam as well as to a main detection beam. Since all main excitation beams and also all main detection beams are quasi-parallel, a good uniform lateral distribution in the object plane is ensured and the detection sites in the middle of the arrangement are comparable with those at the border of the arrangement.

In the present invention a telecentric optical system always has a field lens. In the context of this invention the field lens is a lens which is nearest to the object (with reference to an embodiment of the optical instrument without the objective array according to the invention), through which all excitation light beams and all fluorescence signals pass, which can have one or more components and together with additional optical components of the device contributes to the telecentricity in the object space and/or in the image space of the device. The one or more components (achromatic system) of the field lens can themselves be lens elements which are spatially separated. The field lens determines the field of vision of the optical device.

Within the scope of this invention a telecentric optical system can additionally be an optical system which has a very small aperture and thus a large depth of focus. Therefore, the quality of an excitation optical system or of an imaging optical system in which telecentricity is used in the object space is insensitive to the distance of a certain object point from the optical system. The aperture of a telecentric optical system is imaged at infinity.

The field lens of the present invention transfers excitation light from the light source to the arrangement of a plurality of individual detection sites and transfers fluorescence signals from the arrangement of a plurality of individual detection sites to the optical sensor. This does not exclude the possibility that additional optical components may be introduced into the beam path e.g. between the light source and the field lens, between the field lens and the optical sensor or between the field lens and the arrangement of a plurality of individual detection sites (in particular an objective array according to the invention).

The angle of incidence a is defined as the angle between the quasi-parallel main beams of the excitation light beam and the normals of the interface which, within the scope of this invention, is the support of this arrangement.

According to another embodiment, the present invention relates to an optical instrument for imaging chemiluminescence or bioluminescence signals from an arrangement of a plurality of individual detection sites comprising:
 a holding device for holding a planar support with an arrangement of a plurality of individual detection sites;
 an optical sensor which is arranged such that it receives chemiluminescence or bioluminescence signals from the arrangement of a plurality of individual detection sites and which is designed such that it generates computer-readable primary data;
 a field lens which is arranged such that it transfers chemiluminescence or bioluminescence signals from the arrangement of a plurality of individual detection sites to the optical sensor;
 an imaging lens arrangement which is arranged such that it transfers chemiluminescence or bioluminescence signals from the field lens to the optical sensor;
wherein:
 said instrument comprises an objective array, which comprises a field lens array with field lens array elements and a pupil lens array with pupil lens array elements,
wherein the objective array is disposed in the beam path between the field lens and the arrangement of a plurality of individual detection sites.

Another object of this invention is a real-time PCR instrument comprising
 an optical instrument according to the invention and
 a device for heating and cooling a support with one or more wells each containing a reaction mixture capable of performing a PCR reaction.

Within the scope of this invention the means for heating and cooling include any means which are able to control and change the temperature of the arrangement of a plurality of individual detection sites in a cyclic manner in order to carry out a cyclic PCR amplification of nucleic acids. Such heating and cooling devices are commonly used in thermal cyclers and are well known to the skilled person.

In the present invention an arrangement of a plurality of individual detection sites can summarize individual objects of an assay which are composed of two or more assays which are spatially separated in order to achieve a parallel analysis, for example in a microtitre plate or on a functionalized surface of a glass slide.

Moreover the term beam path is used in the present invention to summarize all areas the light beam passes through on its way from the light source through at least the field lens to the arrangement of a plurality of individual assays and from the arrangement of a plurality of individual assays through at least one field lens to the optical sensor.

Another subject matter of the present invention is a system for simultaneously performing and monitoring one or more PCR reactions in real-time comprising
- a multiwell plate as an arrangement of a plurality of individual detection sites, each containing a reaction mixture capable of performing a PCR reaction,
- fluorescent DNA binding entities, and
- a real-time PCR instrument according to the invention, comprising an optical instrument according to the invention for illuminating the plurality of individual detection sites of the multiwell plate with light, for example with telecentric light, and for detecting the fluorescence signals from each well of the multiwell plate by an optical sensor which is arranged such that it can receive the corresponding fluorescence signals in order to generate computer-readable primary data.

The light source of the PCR instrument can be a LED.

In the present invention the fluorescent DNA binding entities are any fluorescent dyes or arrangements of fluorescent dyes for the real-time detection of amplified DNA which are known to a person skilled in the art and which can be used to detect amplified DNA e.g. double-stranded DNA-specific binding dyes, fluorescently-labelled hybridization probes which only irradiate fluorescence when they bind to their target nucleic acid, TaqMan probes, molecular beacons, single label probes (SLP) or FRET hybridization probes.

Yet a further object of the present invention is a method for amplifying, detecting and/or quantifying a plurality of DNA target sequences comprising:
- providing a composition or reaction mixture which is able to carry out PCR reactions;
- treating the reaction mixture according to a thermocycling protocol such that an amplification of the plurality of DNA target sequences can take place; and
- determining the presence and the number of each DNA sequence at least once after a plurality of amplification cycles using fluorescent DNA binding entities and a real-time PCR instrument according to the invention.

The composition or reaction mixture which is able to carry out PCR reactions comprises within the scope of this invention buffers, nucleotides, enzymes, primers and the fluorescent-DNA binding entities.

A thermocycling protocol is the protocol which defines the cycles and time periods of melting, annealing and amplification temperatures.

The invention is further elucidated in the following on the basis of a non-limiting embodiment example as shown in the Figures. The characteristics described therein can be used individually or in combination with one another in order to create certain embodiments of the invention.

FIG. 1a shows a schematic diagram of an embodiment of an optical instrument 1 for imaging fluorescence signals of a plurality of individual detection sites 2 according to the prior art, for example according to EP 1 681 555 B1 or EP 1 681 556 B1. The optical instrument 1 is used to simultaneously monitor and detect PCR amplifications (polymerase chain reaction amplifications) which take place in the individual wells of a microtitre plate. The wells of a multiwell plate thus form an arrangement of a plurality of individual detection sites 2.

The optical instrument 1 for imaging fluorescence signals from an arrangement of a plurality of individual detection sites 2 comprises a holding device 3 for holding a planar support 4 with an arrangement of a plurality of individual detection sites 2, at least one light source 5 for emitting light at least one excitation frequency, an optical sensor 6 which is arranged such that it receives fluorescence signals 7 from the arrangement of a plurality of individual detection sites 2 and which is designed such that it generates computer-readable primary data, a field lens 8 which is arranged such that it transfers excitation light 9 from the light source 5 to the arrangement of a plurality of individual detection sites 2 and fluorescence signals 7 from the arrangement of a plurality of individual detection sites 2 to the optical sensor 6, an excitation lens array 10 which is arranged such that it transfers excitation light 9 from the light source 5 to the field lens 8, and an imaging lens arrangement 11 which is arranged such that it transfers fluorescence signals 7 from the field lens 8 to the optical sensor 6.

A large number of instruments are known to a person skilled in the art which are able to image fluorescence signals 7. If the optical instrument 1 should be able to simultaneously image the fluorescence signals 7 from an arrangement of the plurality of individual detection sites 2 e.g. the wells of a microtitre plate or the spots of a microarray, it must be ensured that the excitation of the dyes with the excitation light 9 and the imaging of the fluorescence signals 7 in the centre of the arrangement and at the borders of the arrangement are comparable. Moreover, even if the requirement of a homogeneous intensity distribution across the light beam is fulfilled, the alignment of the planar support 4 is still important to ensure that the support 4 as a whole is in the focal plane of the imaging optics and also of the excitation optics. In addition some special problems arise when the support 4 or the plurality of individual detection sites 2 detected by the optical instrument 1 has a depth as in the case of the wells of microtitre plates.

A solution to the above-mentioned problems is to use telecentric optics. In a telecentric optical system the main beams which emanate from the individual object points are quasi-parallel. Actually the main beams would even be strictly parallel if there were no optical aberrations. The latter is then referred to as telecentricity error. Each object point of course does not only see the main beam which comes from the centre of the pupil but also edge beams which come from the edge of the pupil and also beams which are between the edge beam and main beam. Hence, each object point is assigned to a bundle of rays that lies within a cone. The axis of this cone is the main beam. The cone ideally has a small angle of aperture. In fact there are even two cones namely one for the illumination and one for the detection. As a consequence of the telecentric optical systems all object points within a finite field of vision are observed with approximately the same perspective and the same intensity, in other words the telecentric optical systems has a large depth of focus and a uniform excitation or imaging profile.

The properties of an optical system can be characterized by its numerical aperture (NA) which in general should be as large as possible to achieve a high sensitivity and a good imaging resolution:

$$NA = n \cdot \sin \theta$$

wherein n is the refractive index of the medium and θ is the aperture angle.

Several aspects have to be taken into consideration when designing an optical instrument 1 for telecentric excitation of a lateral distribution of detection sites 2 and the telecentric imaging of fluorescence signals 7 from the detection sites 2.

On the one hand, the NA values should be as large as possible because a small NA value for the imaging optics corresponds to a poor imaging resolution and a small NA value for the excitation optics corresponds to a waste of illumination power for the excitation. On the other hand, minimizing the NA value can increase the depth of focus of the telecentric optics which can be important when the arrangement of individual detection sites 2 has a certain depth as in the case of microtitre plates. Moreover, a small NA value is also possible from a commercial point of view because an optical system with a small aperture is generally cheaper to manufacture.

If it is intended to use the telecentric optical instrument 1 for a whole frequency range, the optics should also be achromatic. For the fluorescence imaging itself even more requirements have to be addressed since the fluorescence imaging must have the right scaling for the correct reproduction of the lateral distribution of detection sites 2 on the optical sensor 6. In addition imaging errors such as spherical or chromatic aberration, coma, astigmatism or curvature of field have to be taken into consideration.

There are several ways to create telecentric optics. In general a telecentric optical system is in the form of a multi-element lens where several lenses are arranged successively in the beam path. A telecentric optical system can be designed to be telecentric in the object plane or telecentric in the image plane or telecentric in both planes, a so-called doubly telecentric optical system. Moreover, it is possible to illuminate an object with telecentric light and/or to detect an object in a telecentric manner. In general it is sufficient to provide an optical system with telecentricity in the object plane because this already guarantees a homogeneous illumination of the whole object laterally as well as in the third dimension and the accurate collection of light irradiated from the object.

Within the scope of this invention the excitation of the plurality of individual detection sites 2 as well as the imaging of the fluorescence signals 7 emitted by the plurality of individual detection sites 2 can take place in a telecentric manner.

A central part of all telecentric optics is the field lens 8. This lens is closest to the object and determines the field of vision of the instrument 1. Therefore, the diameter of this lens usually increases when the arrangement of a plurality of individual detection sites 2 is distributed over a large area. Field lenses 8 exist as singlets (one single lens) or as achromats comprising e.g. two lenses glued together. A special field lens 8 that can also be used for this invention is a Fresnel lens. A Fresnel lens has a special complex curvature with multiple tapered regions on at least one optically active surface that provides the same telecentric properties as a field lens 8. In most cases Fresnel lenses have only one surface with multiple tapered regions which is supported by a planar surface perpendicular to the optical axis and therefore they are thinner compared to normal field lenses. So-called free-form lenses can also be used. In practice field lenses are often aspherical in order to minimize the telecentricity error. Normally these aspherical lenses are, however, rotationally symmetrical. The latter is then not a free-form surface.

Especially in the case of wells of a microtitre plate which have a certain depth, a large angle of incidence has the effect that only a part of the inner region of the well is illuminated. Consequently an angle of incidence of less than about 20° is expedient for microtitre plates. In a certain embodiment of the optical instrument 1 the angle of incidence a of the excitation light 9 is less than about 20°, for example less than about 10° or less than about 5°.

It should be noted that on the other hand the angle of incidence a is also limited with regard to smaller values because the finite aperture of both the excitation optics and also of the imaging optics is larger than zero.

In another embodiment of the optical instrument 1 according to the invention the angle of incidence α is:

$$\alpha \geq \theta_1 + \theta_2$$

wherein $\theta_1$ is the aperture half angle of the excitation optics and $\theta_2$ is the aperture half angle of the imaging optics.

The aperture half angle $\theta$ of both the excitation optics and the imaging optics is defined by the corresponding numerical aperture NA as:

$$NA_i = n_i \sin \theta_i,$$

wherein $n_i$ is the refractive index of the medium between the object and the respective optics and wherein i=1 for the excitation optics and i=2 for the imaging optics. If the angle of incidence α becomes smaller than defined by the equation above, an increasing amount of the reflected light of the excitation light beam 9 strikes the optical sensor 6. This statement is true for an arrangement of functionalized spots on a planar, solid support 4 and also for a microtitre plate.

In another embodiment, the optical instrument 1 according to the invention additionally comprises an excitation filter system 12 capable of transferring at least one excitation frequency from the light source 5 to the arrangement of a plurality of individual detection sites 2 while blocking a plurality of other frequencies and/or an imaging filter system 13 capable of transferring fluorescence signals from the arrangement of a plurality of individual detection sites 2 to the optical sensor 6 while blocking light of the excitation frequencies.

As already stated the optical instrument 1 comprises an excitation lens arrangement 10 which transfers light from the light source 5 to the field lens 8. This means that the light of the light source 5 is imaged on the arrangement of a plurality of individual detection sites 2 with the aid of excitation optical system comprising the field lens 8 and an excitation lens arrangement 10. The excitation optical system provides a telecentric excitation light 9 on the object side of the field lens 8 and is therefore a telecentric excitation optical system. The excitation lens arrangement 10 comprises at least one lens, for example at least three lenses, in order to increase the aperture of the excitation with regard to a better utilization of the light source power. The excitation lens arrangement 10 can comprise an aspherical lens if the number of lenses should be reduced. The telecentric excitation optical system are designed to be achromatic in order to achieve a homogeneous intensity distribution across the arrangement of a plurality of individual detection sites 2 independently of the excitation wavelength.

The light source 5 can be a light source which emits light having a plurality of frequencies for example a white light source, a gas discharge lamp, a Xenon lamp, a mercury lamp, a filament lamp or a tungsten lamp. The light source 5 can also only emit light of a single frequency or in a narrow frequency range, for example a laser or an LED. The light source 5 can also comprise a combination of more than one illuminant. In addition filters or sets of filters may also be used.

The telecentric excitation optical system can, in addition to the field lens 8, the excitation filter system 12 and the excitation lens arrangement 10, comprise several additional components. In one embodiment the telecentric excitation optical system additionally comprises a light guide in order to transfer the light from the light source to the optical components of the optical system. Using a light guide it is possible to couple light from different light sources 5 and transfer this combined light simultaneously to the optical components. The direction of the excitation light 9 and/or of the fluorescence signals 7 can be changed by a mirror or beam splitter 14 or a light deflecting unit. In addition a light mixer (e.g. a light mixing rod) may be provided.

The light from the light source 5 is imaged onto the arrangement of a plurality of individual detection sites 2 using the telecentric excitation optical system comprising the field lens 8 and the excitation lens arrangement 10. Hence, in this embodiment of the invention the excitation of the plurality of individual detection sites is carried out with an excitation optical system which can be telecentric in the object space.

Figure 1B:
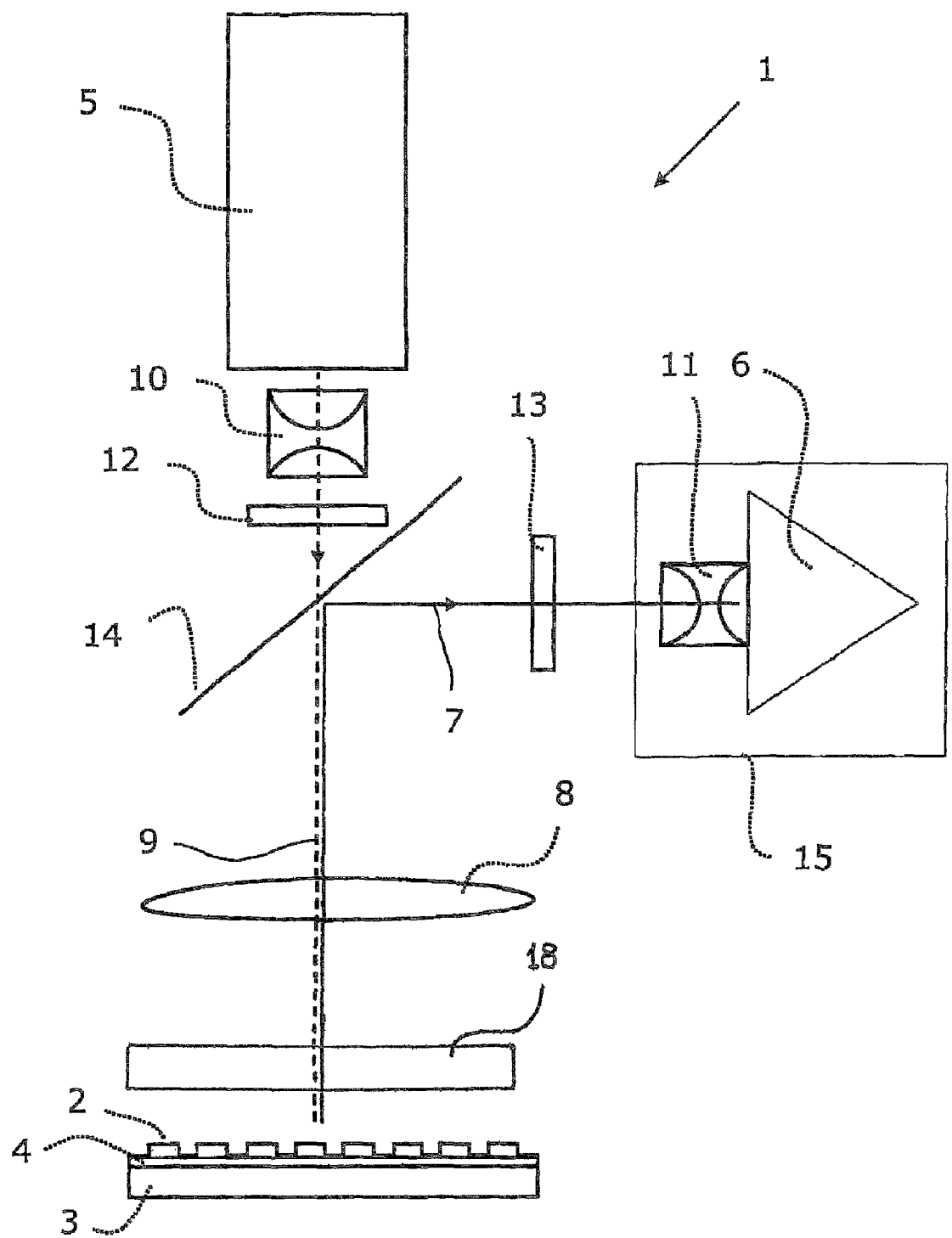
FIG. 1b shows a schematic diagram of an embodiment of an optical instrument according to the invention.

The optical instrument 1 of FIG. 1b can also be adapted to imaging chemiluminescence and bioluminescence signals. Since, in these cases no excitation light 9 is required, the light source 5, the excitation lens arrangement 10 and the excitation filter system 12 can be omitted. The further design can take place as in an optical instrument 1 for imaging fluorescence signals 7.

The optical instrument 1 of FIG. 1b comprises an imaging lens arrangement 11 which transfers light from the field lens 8 to the optical sensor 6. This means that the fluorescence signals 7 which are generated on the arrangement of a plurality of individual detection sites 2 are imaged onto an optical sensor 6 by a telecentric imaging optical system comprising a field lens 8 and an imaging lens arrangement 11. In other embodiments of the invention the telecentric imaging optical system additionally comprises for example a light beam folding unit and/or special imaging filter systems 13.

The telecentric imaging optical system should be optimized to the size of the optical sensor 6 and the spatial dimensions of the arrangement of a plurality of individual detection sites 2. As in the case of the excitation lens arrangement 10, the imaging lens arrangement 11 comprises at least one lens, for example an arrangement of at least five lenses. A large number of lenses is advantageous for the imaging lens arrangement 11 because, in comparison to the excitation optical system, even higher requirements have to be taken into consideration for the imaging optics. The fluorescence image must have the right scale for the correct reproduction of the lateral distribution of detection sites 2 on the optical sensor 6. In addition imaging errors such as spherical or chromatic aberration, coma, astigmatism, special errors or curvature of field have to be taken into consideration. Due to the imaging of the fluorescence signals 7 onto the optical sensor 6, the fluorescence imaging can be carried out with an imaging optical system which is only telecentric on the object side of the field lens 8. The imaging lens arrangement 11 can be coupled to the optical sensor 6 to form an imaging unit 15.

Another embodiment of the optical instrument 1 according to the invention is an optical instrument wherein the individual detection sites 2 of the arrangement are spots on a planar support 4 and the fluorescent dyes are applied to these spots. An example of this particular embodiment of the optical instrument 1 is a device for simultaneously imaging fluorescence signals 7 from various spots of a planar arrangement. In a specific embodiment such an arrangement is a DNA arrangement where laterally restricted areas are functionalized with DNA probes which have different sequences. In this case the optical instrument 1 according to the invention can monitor hybridization events with samples which contain nucleic acid if for example the complementary DNA strand is labelled with a fluorescent dye. As an alternative to labelling the DNA molecules in the sample, the hybridization events can also, be visualized by fluorescent dyes that bind to double-stranded nucleic acids.

The telecentric excitation optical system in the embodiment example of FIG. 1b operates for example at frequencies of 450 nm to 650 nm and the telecentric imaging optical system operates at frequencies of 500 nm to 740 nm. In the embodiment example the light source 5 is a Xenon lamp and a cooled ⅔ inch CCD chip with 1024×1344 pixels serves as an optical sensor 6. The optical instrument 1 is designed to image an area of 83 mm×117 mm in such a manner that microtitre plates with 96 wells (spacing 9 mm, diameter 5 mm) and 384 wells (spacing 4.5 mm, diameter 3 mm) can be used. The suitable wavelength for excitation and imaging for particular fluorescent dyes is adjusted by means of filter wheels.

In the embodiment example the telecentric excitation optical system has a numerical aperture of 0.35 on the side of the light source 5 and of 0.014 on the side of the microtitre plate. For geometric reasons the light source 5 is arranged perpendicular to the CCD chip and the excitation light beam 9 is aligned in the direction of the microtitre plate using an additional mirror. The excitation light beam 9 itself has an angle of incidence to the microtitre plate of 2° and an intensity fluctuation over the object field (88 mm×122 mm) of less than about 10%. The "excitation light beam 9" in this case is synonymous for the "optical axis of the illumination" because the beam path comprises a large number of beams and not only one. The imaging optical system also has a diaphragm of 0.014 on the object side and an imaging scale of 0.075 with a distance of 800 mm between the object and image. This large distance can be achieved using two folding mirrors. The imaging optical system has a depth of focus of ±3 mm.

An insofar known instrument 1 according to FIG. 1b utilizes the radiant power of the light source 5 to very inefficiently excite the fluorescence of the detection sites 2 because essentially the area around the detection sites 2, for example the solid part of the heating cover of a microtitre plate, is illuminated. Only the light which falls on the detection sites 2 for example through the holes provided for this in the heating cover of a microtitre plate is actually available for fluorescence excitation. This is illustrated on the basis of FIG. 2.

Figure 2:
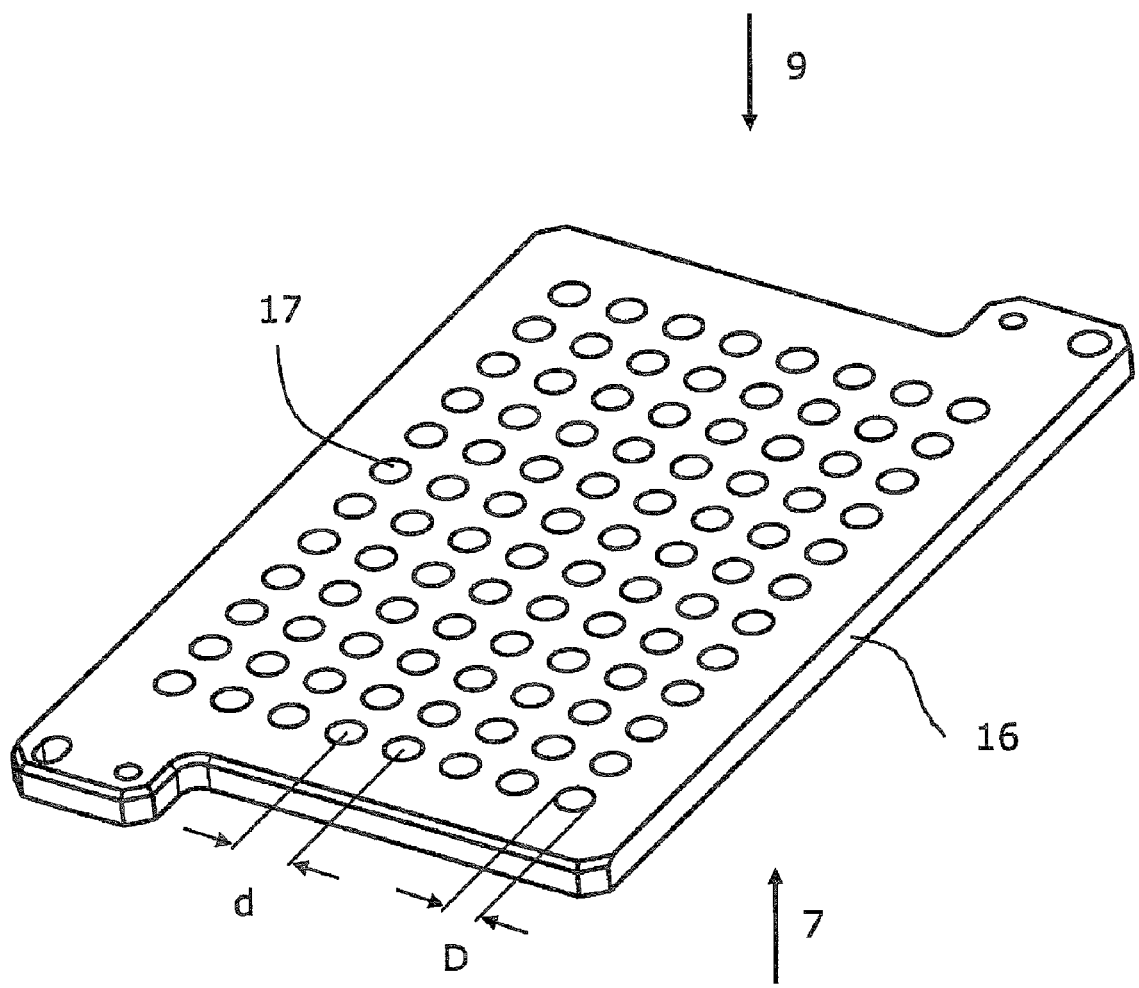
FIG. 2 shows a heating cover of a PCR multiwell plate with holes for illumination and for the optical analysis of the samples in the wells.

FIG. 2 shows such a heating cover 16 which is located on the upper side of the wells of a microtitre plate. It is usually non-transparent and has a hole 17 for each well through which the solution in the well is illuminated with excitation light 9 and through which the fluorescence signals 7 emitted from the solution are detected.

The distance between the holes d in the heating cover 16 is for example 9 mm according to the SBS microtitre standard format. The hole diameter D of 5.2 mm is a little less than the diameter of the cylindrical part of wells of 5.5 mm and considerably smaller than the distance between the holes d. The light lost by shadowing by the non-transparent parts of the heating cover 16 can be calculated as follows from the distance between the holes d and the hole diameter D.

The area $A_L$ of a hole 17 is:

$$A_L = \left(\frac{D}{2}\right)^2 \cdot \pi = 21.24 \text{ mm}^2$$

Each hole 17 in the heating cover 16 can be assigned to a square whose edge length is exactly the distance d between the holes and wherein neighbouring squares adjoin each other without intermediate spacing. The area $A_Q$ of this square is:

$$A_Q = d^2 = 81 \text{ mm}^2$$

The proportion $\eta_A$ of the excitation light 9 used for illumination is the ratio of $A_L$ to $A_Q$:

$$\eta_A = \frac{A_L}{A_Q} = 26.2\%$$

The value of $\eta_A$ is thus purely determined by geometric proportions and can be interpreted as a "filling factor". This filling factor and thus the efficiency of the fluorescence excitation of the detection sites 2 are improved by the objective array according to the invention.

In addition to the efficiency of the fluorescence excitation, the invention also improves the efficiency of the fluorescence detection because an optical instrument 1 according to the prior art also only inefficiently utilizes the radiation flux of the fluorescence signals 7 to the optical sensor 6. The fluorescent light emitted from the dye molecules at the detection site 2 is namely irradiated in a spatially isotropic manner. Only a small part of this light is detected by the detection optics and directed onto the detector 6. The numerical aperture of a detection optical system of FIG. 1b is minute and is typically NA=0.014. The relationship between the numerical aperture NA of the detection optics and the solid angle $\Omega_D$ detected by these optics is:

$$\Omega_D = 2\pi \cdot (1 - \sqrt{1-NA^2}) = 6.2 \cdot 10^{-4}$$

The complete solid angle $\Omega$tot which is illuminated by the fluorescence radiation is $4\pi$. Thus, the portion $\eta_D$ of the fluorescence light utilized for the measurement with the optical sensor 6 is only about 0.005%:

$$\eta_D = \frac{\Omega_D}{\Omega_{tot}} = 0.5 \cdot (1 - \sqrt{1-NA^2}) = 4.9 \cdot 10^{-5}$$

The invention improves the efficiency of the fluorescence excitation as well as the efficiency of the fluorescence detection. This is achieved by placing an objective array 18 between the field lens 8 and the heating cover 16 or the arrangement of a plurality of individual detection sites 2.

Figure 3:
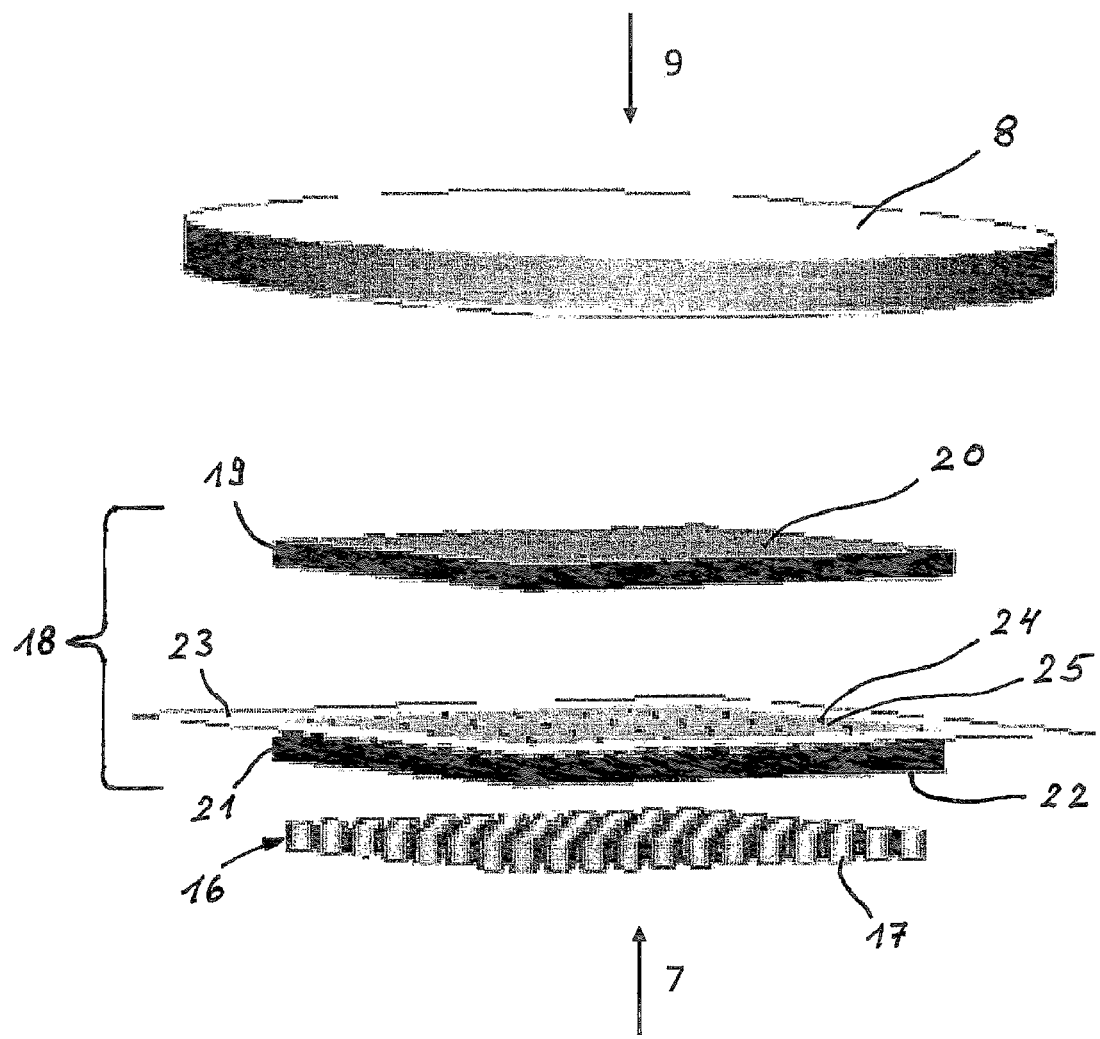
FIG. 3 shows a schematic exploded view of an embodiment of certain elements of the optical instrument according to the invention.

The components and the position of the objective array 18 are shown in FIG. 3. The objective array 18 comprises a field lens array 19 with field lens array elements 20 and a pupil lens array 21 with pupil lens array elements 22 and is situated in the beam path between the field lens 8 and the arrangement of a plurality of individual detection sites 2. The objective array 18 can thus be referred to as an array objectives. The field lens array 19 faces the field lens 8 and the pupil lens array 21 faces the plurality of individual detection sites 2. The field lens array 19 is arranged parallel to the pupil lens array 21. In the embodiment example the optical instrument 1 thus has a number of optical channels which corresponds to the number of wells of the microtitre plate where each optical channel comprises a dedicated field lens array element 20 and a dedicated pupil lens array element 22.

The object plane is, as is the case with the optical instrument 1 according to the prior art, for example the underside of the heating cover 16 which faces the wells. This object plane forms a field plane where the field plane conjugated thereto lies in the field lens array element 20 i.e. on the surface of the field lens array element 20 which faces away from the pupil lens array element 22. The field planes of the field lens 8 or of the field lens array element 20 and of the heating cover 16 remain conjugated to one another even with the objective array 18 according to the invention. Expressed more exactly the field lens 8 alone does not have a field plane, but rather the detection optical system (imaging lens arrangement 11) together with the field lens 8. Both together form an image of the upper side of the field lens array 19 on the optical sensor 6 and not the field lens 8 alone. This applies correspondingly to the illumination branch.

Figure 4:
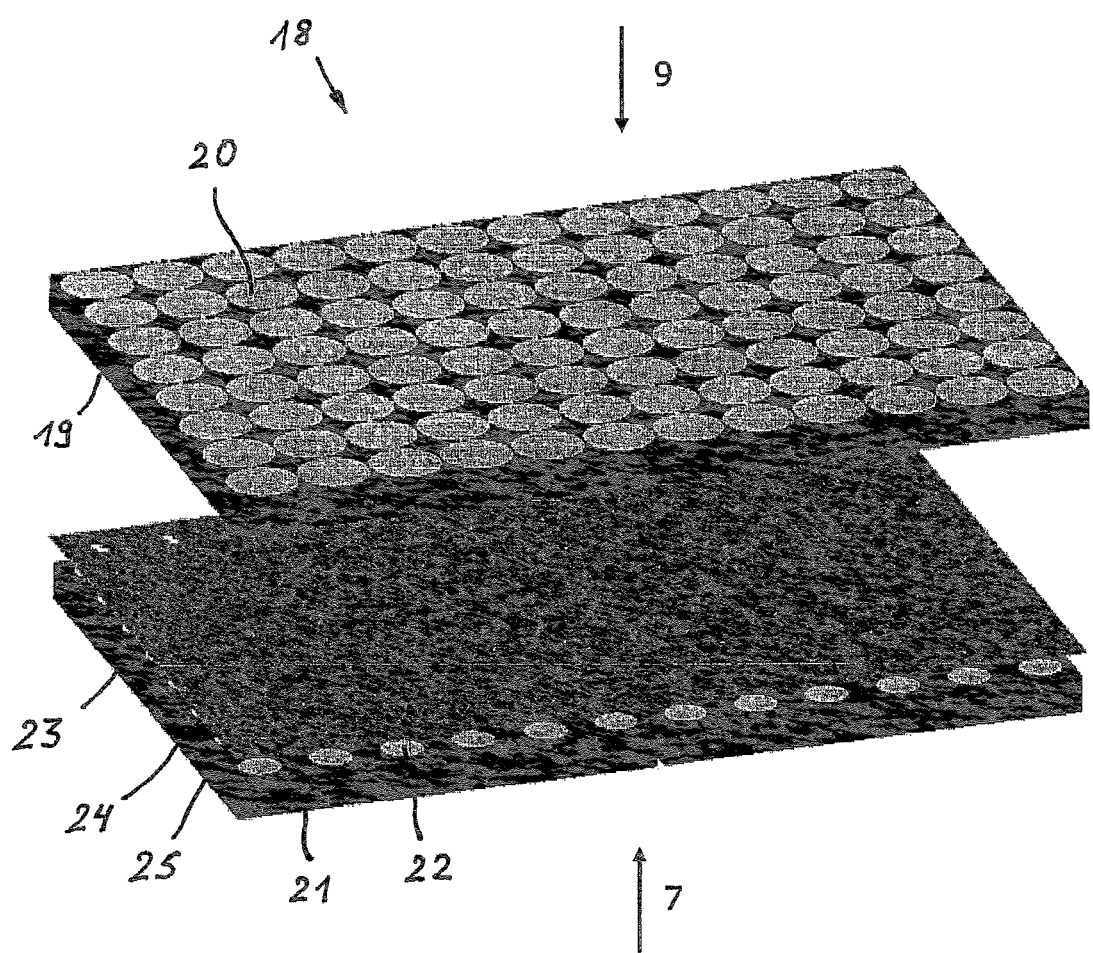
FIG. 4 shows an objective array according to the invention consisting of a field lens array, diaphragm array and pupil lens array.

FIG. 4 shows an objective array 18 according to the invention consisting of a field lens array 19 and pupil lens array 21 where in a certain embodiment an diaphragm array 23 is arranged between the field lens array 19 and pupil lens array 21. A two-lens objective comprising a field lens array element 20 and a pupil lens array element 22 are in each case allocated to each well of the microtitre plate or each hole 17 in the heating cover 16. The objectives are identical to one another. Thus, in the field array optical arrangement 18 a lens pair formed in each case from a field lens array element 20 and a pupil lens array element 22 is allocated to one of the detection sites 2 in each case.

The microtitre plate and the heating cover 16 are removed from their original position relative to the field lens 8 (displaced by about 60 mm) compared to the prior art due to the objective array 18 placed between them and placed in the image plane (in relation to the illumination with the excitation light 9) of the 96 objectives of the objective array 18. As in the prior art the original position of the underside of the heating cover 16 can be selected as the object plane (with reference to the detection of the fluorescence signals 7) of the 96 objectives of the objective array 18. These objectives of the objective array 18 improve, on the one hand, the filling factor of the illumination and, on the other hand, they enlarge the numerical aperture of the detection. This is illustrated in the following on the basis of FIG. 5 to 8.

FIGS. 5 and 6 each show a single channel of the 96-channel objective array 18 consisting of a field lens array element 20, a pupil lens array element 22 and an aperture of the diaphragm array 23 which is located between both lenses near to the pupil lens array element 22. The beam path for fluorescence excitation with the excitation light 9 is drawn in FIG. 5. FIG. 6 shows the beam path for the fluorescence detection of the fluorescence signals 7. In each case one pupil lens array element 22 of the pupil lens array 21 forms an image of a field lens array element 20 of the field lens array 19 (or the edge of a field lens array element 20) on one of the detection sites 2 (i.e. on the lower edge of a hole 17 in the heating cover 16) which are located in the figures at the lower end and form a field plane there. The respective associated hole 17 in the heating cover 16 which is not shown in FIGS. 5 and 6 extends from the field plane on the detection sites 2 upwards towards the pupil lens array element 22. FIGS. 5 to 7 show that the arrangement of pupil lens array element 22 and field lens array element 20 optically conjugates the diaphragm array element 23 with the diaphragms of the illumination (6) and detection (5) systems.

The field lens 8 which is not shown is located above the field lens array elements 20 i.e. on the entry side of the field lens array elements 20 with respect to the excitation light 9 and on the exit side of the field lens array elements 20 with respect to the fluorescence signals 7. Here, i.e. above the field lens array elements 20, the main beams run parallel and the axes of the beam bundles are parallel i.e. the arrangement is telecentric in this region. The field lens array elements 20 of the field lens array 19 generate illumination pupils for the excitation light 9 and detection pupils for the fluorescence signals 7. The objective array 18 images fields (objects, images) as well as diaphragms (pupils). When designing a composite optical system one should take into consideration the imaging of the fields as well as the imaging of the pupils.

On the entry side (top of FIG. 6) the axes of the bundles of rays for the fluorescence detection are parallel to one another and also parallel to the optical axis. The bundles of rays for the fluorescence excitation are also parallel to one another on the entry side (top of FIG. 5) but are slightly tilted with respect to the optical axis in contrast to fluorescence detection. The tilting is selected such that the bundles of rays for the fluorescence excitation and fluorescence detection do not penetrate the field plane (object plane, at the detection sites 2) (see also FIG. 10) in order to achieve a separation between the excitation light 9 and fluorescence signals 7.

Of course it is also possible to make a converse arrangement such that the fluorescence excitation is tilted with respect to the optical axis and the fluorescence detection takes place at an angle to the optical axis, or the fluorescence excitation as well as the fluorescence detection can be carried out at a different angle to the optical axis. The beam directions on the entry side for the fluorescence excitation and the fluorescence detection are predetermined by the optical system of the instrument 1. They are formed by the laterally separated diaphragms of the illumination beam path and of the detection beam path in the optical instrument 1. Usually it is advantageous to select the main beams of detection such that they are parallel to the optical axis. A breach of symmetry usually results in an impairment of the imaging performance. A good imaging performance is in practice necessary more for the detection than for illumination.

FIG. 7 shows in a combination of FIGS. 5 and 6 a section through a channel of an objective array 18 according to the invention with a diaphragm of the diaphragm array 23 comprising two separate diaphragm openings 24, 25, one for the fluorescence excitation with the excitation light 9 and one for the fluorescence detection of the fluorescence signals 7. The beam paths for fluorescence excitation and for fluorescence detection are shown together. The diaphragm 23 between the field lens array element 20 and the pupil lens array element 22 has two separate diaphragm openings 24, 25 per channel in this embodiment example. One can, however, also provide only one diaphragm opening for each channel (see above). The outer-axial diaphragm opening 24 (left) allows the excitation light 9 for fluorescence excitation to pass. The axial diaphragm opening 25 (right) allows the fluorescence signals 7 to pass for fluorescence detection. Also the diaphragm opening 24 allows the detection light to pass because the fluorescence source irradiates in an isotropic manner. However, this light is absorbed at the latest on the diaphragm of the detection optics. The detections sites 2 i.e. the holes 17 in the heating cover 16 are imaged by the pupil lens array elements 22 in a format filling manner (i.e. accurate to shape and size) on the upper side of the field lens array elements 20. Thus, these upper sides and the holes 17 in the heating cover are optically conjugated.

The ratio of the distance between the holes d to the hole diameter D of the heating cover 16 is for example selected for the imaging scale $\beta$ of the 96 objectives:

$$\beta = d/D = 1.73$$

In general it is advantageous when the plurality of detection sites 2 have a diameter D and are arranged at a distance d to one another where the imaging scale $\beta$ of the pupil lens array elements 22 is equal to the ratio of the distance d to diameter D. Thus, each individual two-lens objective of the objective array 18 forms an image of the associated hole 17 of the heating cover 16 where the image has a size D. From the view point of the illumination optics the holes 17 in the heating cover 16 then appear enlarged by the imaging scale $\beta$ and the interspaces between the images of the holes 17 appear to be shrunk together to such an extent that they are just tangentially touching each other.

Figure 8:
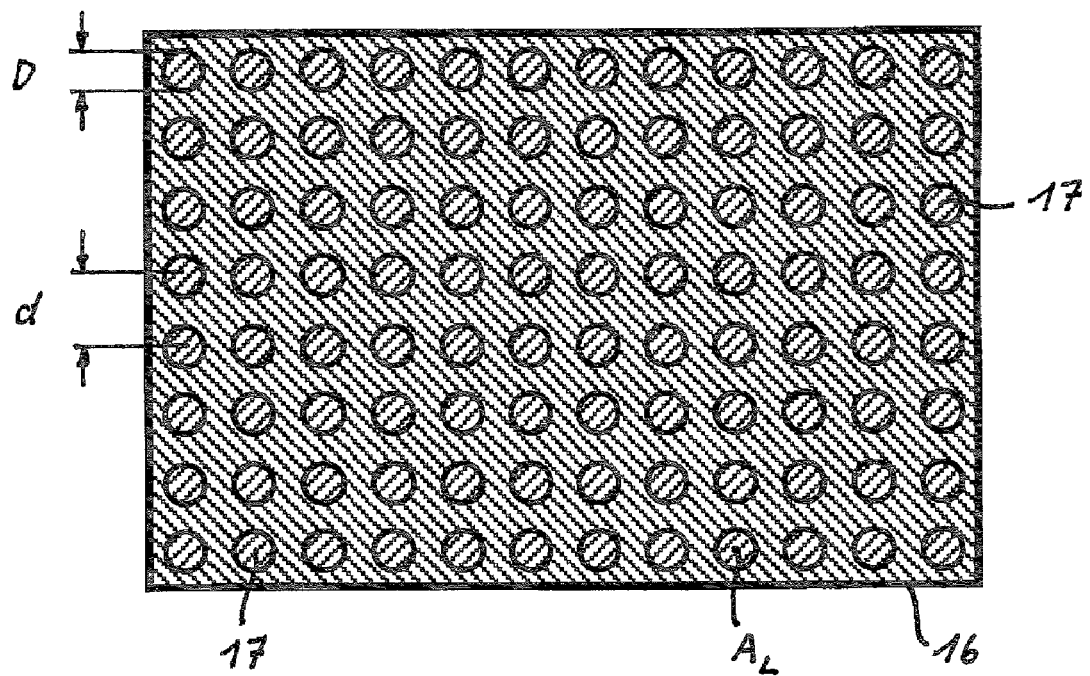
FIG. 8 shows a top-view of the heating cover of FIG. 2 as an object for imaging by the objective array.
Figure 9:
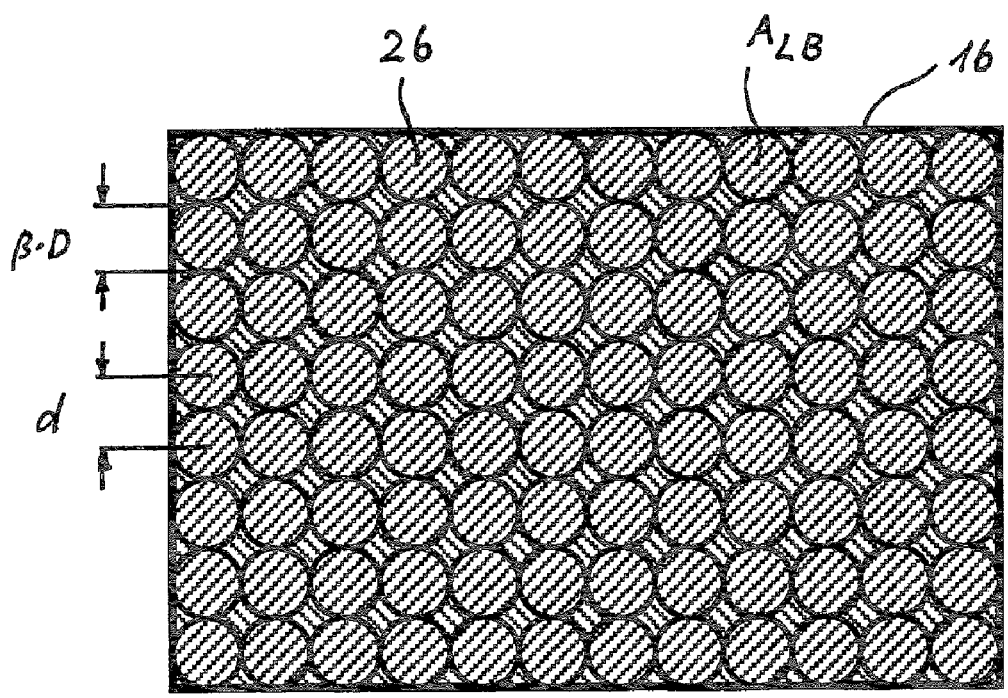
FIG. 9 shows the image of the heating cover of FIG. 8 after imaging by the objective array.

FIG. 8 shows a top-view on the heating cover 16 of FIG. 2 as an object for imaging by the objective array 18, FIG. 9 shows the image of the heating cover 16 of FIG. 2 after imaging by the objective array 18. The fact that only the holes 17 appear to be enlarged, but not also at the same time the distances between them is because this is not scaled imaging with an objective but rather imaging with an optical array. The optical array of the objective array 18 thus only generates a magnified image of the holes 17 without changing the distance d between them. Since the image is magnified by the imaging scale $\beta$, the area $A_{LB}$ of a hole image 26 in FIG. 9 is:

$$A_{LB} = \left(\frac{d}{2}\right)^2 \cdot \pi = 63.62 \text{ mm}^2 = \beta^2 \cdot A_L$$

The proportion $\eta'_A$ of the utilized excitation light 9 is the ratio of ALB to AQ:

$$\eta'_A = \frac{A_{LB}}{A_Q} = 78.5\%$$

The gain factor $g_A$ of the objective array 18 for fluorescence excitation is the ratio of $\eta'_A$ to $\eta_A$:

$$g_A = \frac{\eta'_A}{\eta_A} = \frac{A_{LB}}{A_L} = \beta^2 = 3.0$$

The gain factor $g_D$ of the objective array 18 for fluorescence detection results from the following consideration. The numerical aperture NA in the object plane of the detection optics of the optical instrument 1 is 0.014. This plane is imaged by the objective array 18 on the underside of the heating cover in 96 separate channels. In this direction the objective array 18 has a scaling down effect. Correspondingly the numerical aperture NA' on the underside of the heating cover 16 is larger by a factor equal to the imaging scale $\beta$ than in the object plane of the detection optics of the optical instrument 1:

NA'=$\beta$·NA

The solid angle $\Omega'_D$ detected with the aid of the objective array 18 of the detection optics is:

$$\Omega'_D = 2\pi \cdot (1 - \sqrt{1 - NA'^2}) = 1.8 \cdot 10^{-3}$$

The proportion $\eta'_D$ of the fluorescence light utilized by the objective array 18 is thus:

$$\eta'_D = \frac{\Omega'_D}{\Omega_{tot}} = 1.5 \cdot 10^{-4}$$

The gain factor $g_D$ of the objective array 18 for fluorescence detection is the ratio of $\eta'_D$ to $\eta_D$:

$$g_D = \frac{\eta'_D}{\eta_D} = 3.0$$

The total gain factor $g_{tot}$ of the objective array 18 is the product of the gain factors for fluorescence excitation $g_A$ and for fluorescence detection $g_D$:

$$g_{tot}=g_A \cdot D=9.0$$

A simple transformation shows that the gain factor $g_{tot}$ of the objective array 18 can also be written as $$g_{tot}=(d/D)^4=(9.0/5.2)^4=9.0$$

It is thus only dependent on geometric quantities, namely on the hole diameter D and distance between the holes d of the heating cover 16.

The objective array 18 increases the filling factor (packing density), in the current example by a factor of 3 relative to the illumination of the wells with the excitation light 9. Furthermore the objective array 18 increases the numerical aperture, in the present example by a factor of $\sqrt{3}$ with reference to the detection of the fluorescence signals 7. The gain is, however, approximately proportional to the square of the numerical aperture. This then results in a three-fold gain in the detection. Both together result in a signal gain of the fluorescence measurement with the optical instrument 1 which in the present example is by a factor of 9.

When calculating the gain factor $g_{tot}$, it is implicitly assumed that the imaging of the objective array 18 occurs without vignetting. In this case freedom from vignetting means that all beams of the illumination and detection optics of the optical instrument 1 must pass through the objective array 18 without any shadowing of useful light in the beam path. This of course also applies to other light (scattered light, interfering light) which is shadowed by the heating cover 16 or by the diaphragm array 23.

Figure 10:
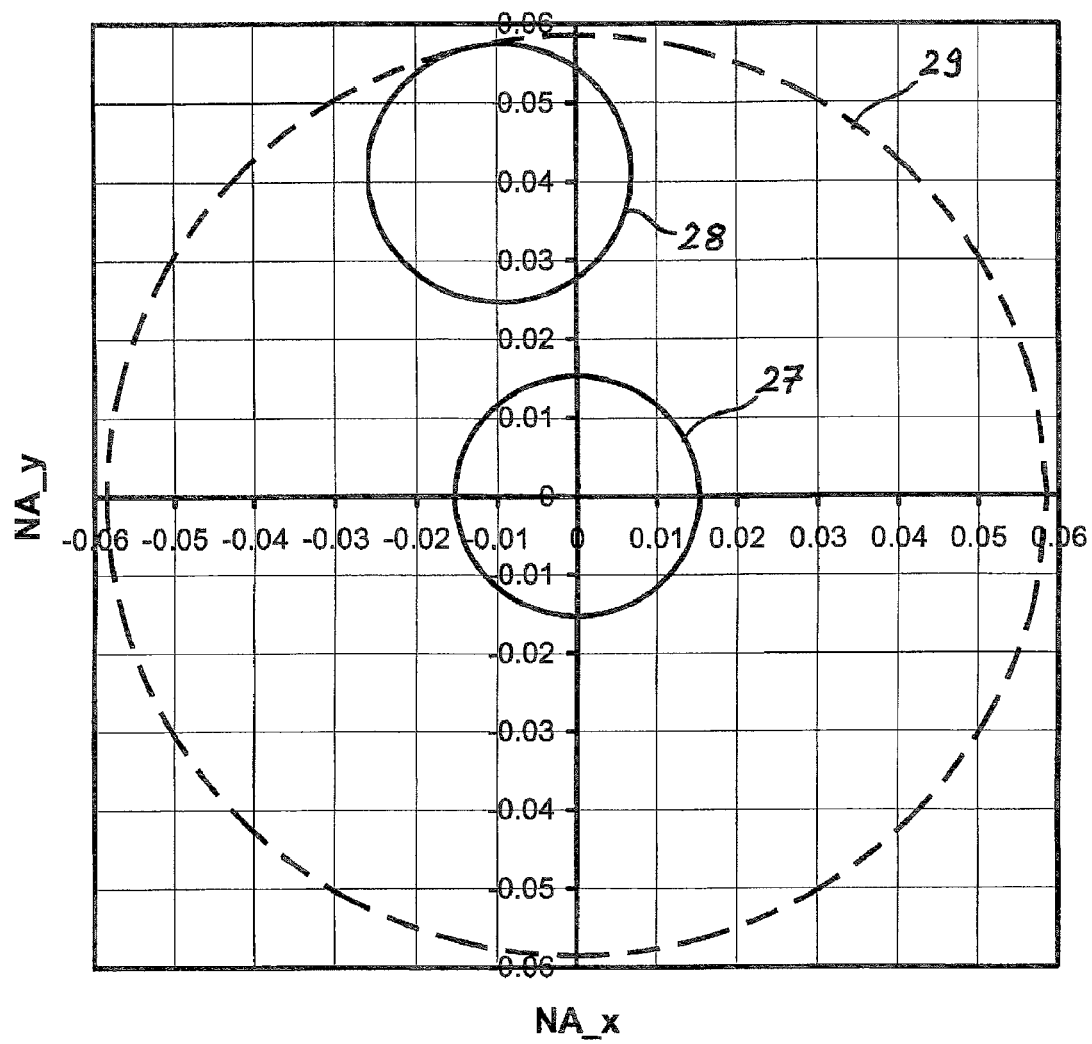
FIG. 10 shows the beam directions of the detection optics and of the illumination optics at the site of the field lens array as well as the envelope of all directions of the objective array.

FIG. 10 shows the beam directions of the illumination and detection optics of the optical instrument 1 in a sinus grid. The sinus grid enables a direct interpretation of the beam directions as a numerical aperture. The beam directions at the position of the field lens array 19 are shown. At the position of the heating cover 16 (or of the detection sites 2) these beam directions again look different. In particular they are then field-dependent (or also location-dependent). Since the illumination and detection optics of the optical instrument 1 are telecentric, the beam directions shown in FIG. 10 are field-independent within the limits of aberrations. For one channel of the objective array 18 all beam directions of the detection system for the fluorescence signals 7 are within the axial curve 27 (FIGS. 6 and 10) and all beam directions of the illumination system for the excitation light 9 are within the outer-axial curve 28 (FIGS. 5 and 10). The curves 27, 28 themselves are defined by the edge of the diaphragm. The dashed curve represents the envelope 29 centered around the optical axis for all beams of all channels of the total objective array 18. The respective numerical aperture of the envelope 29 is 0.059.

The regions enclosed by both curves 27, 28 do not touch or overlap but are rather spaced apart. Due to this fact it is possible to separate the excitation light 9 from the fluorescence signals 7. This according to WO 99/60381 is not the case in the prior art because there the regions of the two corresponding curves 27, 28 completely overlap.

The objective array 18 operates free from vignetting if its numerical aperture on the entry side is larger than the numerical aperture of the envelope 29 (in this case 0.059) and simultaneously when the pupil position on the entry side is telecentric. The telecentricity on the entry side of the objective array 18 is achieved by placing a diaphragm (diaphragms 24, 25 or diaphragm array 23) in the rear focal plane of the front lens (field lens array element 20) of the objective array 18.

The relationship between the numerical aperture NA of a beam, the beam height h (distance from the optical axis measured at the penetration point in a plane perpendicular to the optical axis) in the diaphragm plane and the focal length f of the front lens (field lens array element 20) is:

$$f=h/NA$$

The maximum beam height h in the diaphragm plane should be less than half the hole spacing d/2 in order to avoid a spatial penetration of neighboring channels of the objective array 18.

$$h<d/2$$

Correspondingly the requirement for the focal length of the front lens (field lens array element 20) should be:

$$f<d/2 \cdot NA=76.3 \text{ mm}$$

In some embodiments it may be expedient when the focal length of the field lens array elements 20 is so small that the diaphragm images of the first and second diaphragm apertures 24, 25 do not overlap for a detection site 2 in order to enable a separation of the excitation light 9 and fluorescence signals 7. Furthermore, it may be expedient in some embodiments when the focal length of the field lens array elements 20 is so small that the diaphragm images of neighboring channels (neighboring detection sites 2) do not overlap in order to suppress interfering light. Due to the periodicity of the objective array 18 it is possible that on the entry side bundles of rays on the right edge and left edge coincide.

Figure 11:
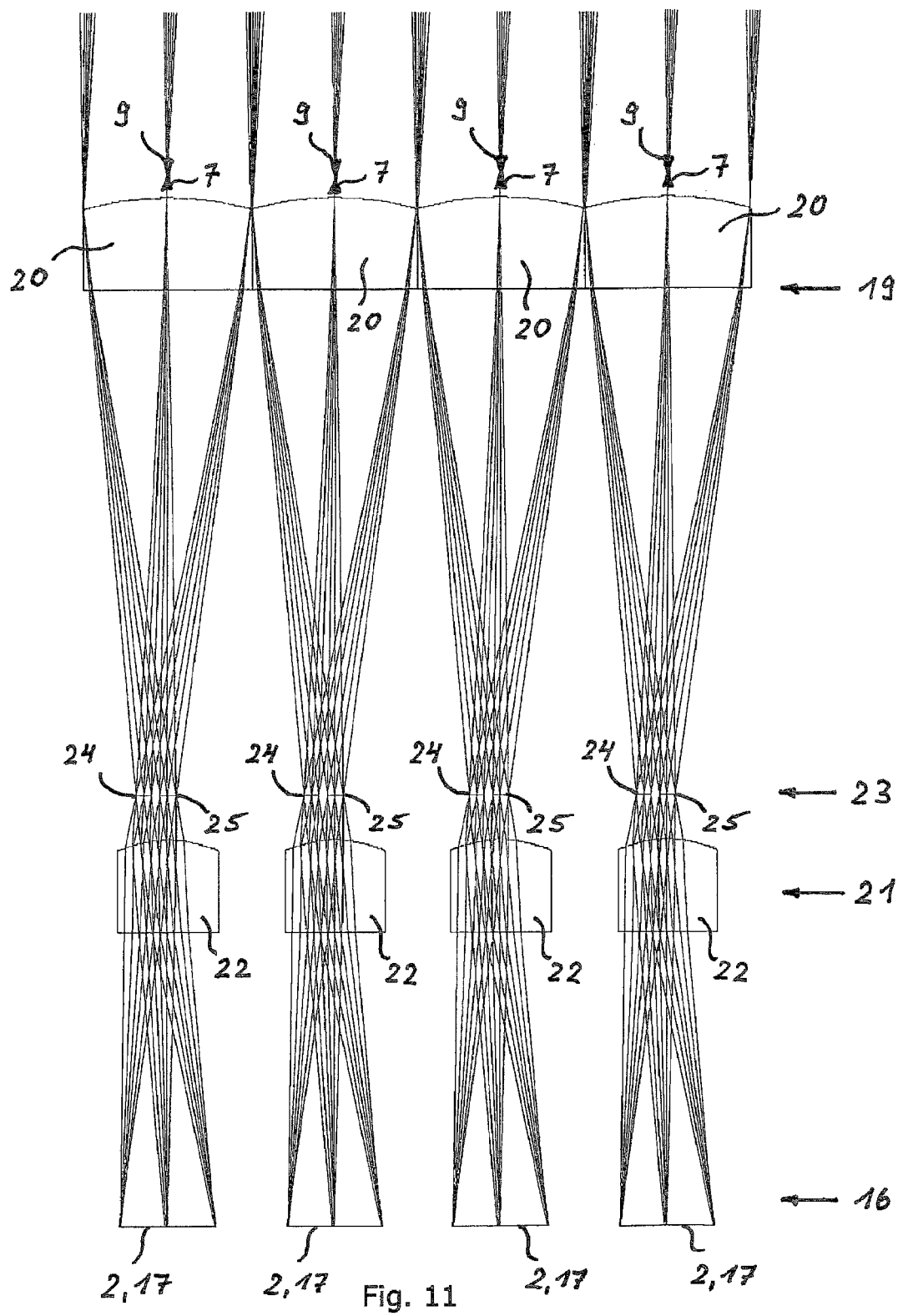
FIG. 11 shows a section of four neighboring channels of the objective array showing the bundles of rays from in each case three field points.

FIG. 11 shows how the front lenses (field lens array elements 20) separate the directly adjacent right edge bundles and left edge bundles and deflect the rays spatially separated in the direction of the respective diaphragm. Since these front lenses (field lens array elements 20) are directly situated in the field plane of the illumination and detection optics of the optical instrument 1, one refers to these quite generally as field lenses and in this case as field lens array elements 20. In other words near-field lenses (i.e. near to the field hence near to the object or image) are referred to as field lenses and near-pupil lenses are referred to as pupil lenses. A field plane is a plane which is illuminated or imaged i.e. an object, an image or an intermediate image. Pupils are diaphragms or images of diaphragms. Field lenses form an image of pupils and pupil lenses form images of fields. The field lens array 19 is near to the field and the pupil lens array 21 and the diaphragm array 23 are near to the pupils.

The field lens array elements 20 do not contribute significantly to the total refractive power of the objective array 18 due to their position near to the field and their comparably large focal length i.e. they do not change the position and size of the image or only to an insignificant extent. Their central function is rather to spatially separate the optical channels i.e. they form pupils for the beam path by means of which the pupil position is adjusted and the angle of the rays is limited. The field lens array elements 20 can provide a telecentric optical system (in FIG. 11 top: telecentric, bottom: not telecentric as elucidated above) on the exit side (at the observation position, on the side of the detection sites 2) i.e. the image of the diaphragms is at infinity. A pupil is an image of an aperture diaphragm. In an optical system there are entrance pupils and exit pupils. If their images are at infinity, the optical system is denoted telecentric on the entry and exit side. Each field lens array element 20 produces in its diaphragm plane an outer-axial image of the diaphragm of the illumination system and an axial image of the diaphragm of the detection system. These images are separated by channels.

Almost the entire refractive power of a lens pair of the objective array 18 is concentrated in each case in the rear lens (pupil lens array element 22). Since they are located near to the pupil, one also refers to them quite generally as pupil lenses or in this case as a pupil lens array element 22. The pupil lens array elements 22 form an image of the edges of the field lens array elements 20 which is true to shape on the lower edges of the holes 17 of the heating cover 16. The holes 17 in the heating cover 16 thus act as an array of field diaphragms.

In each case a diaphragm array element (diaphragm opening, diaphragm) is placed in the focal diaphragm plane of the field lens array elements 20 and the diaphragm array elements mask the images of the diaphragm of the illumination system and the images of the diaphragm of the detection system. The entirety of these diaphragm array elements form a diaphragm array 23. "Masking" in this sense means that the diaphragm array 23 forms a mask or screen where each diaphragm array element has one or more diaphragm openings, is allocated in each case a field lens array element 20 and a pupil lens array element 23 and forms a mask for the beam path through the respective field lens array element 20 and pupil lens array element 23 (i.e. for each "channel" of the objective array 18). This masking is accurate to shape in the embodiment example of FIGS. 2 to 12 i.e. the shapes of the two openings of the diaphragm array elements correspond to the shapes of the images of the diaphragms of the excitation lens arrangement 10 and of the imaging lens arrangement 11. In other embodiments the shape of the diaphragm array elements can also correspond to the shape of the field lens array elements 20 and/or the pupil lens array elements 23 and/or the detection sites 2 (holes 17 in the heating cover 16).

In an other embodiment, the masking can also be actual size. In this case the size of the diaphragm array elements for example corresponds to the size of the illumination pupils of the excitation light 9 and/or to that of the detection pupils of the fluorescence signals 7 and/or the pupils of the detection sites 2 (holes 17 in the heating cover 16).

However, the masking does not necessarily have to be true to shape and/or actual size. For example the diaphragm openings (diaphragm array elements) may also not be circular. Thus, for example the two diaphragm images (image of the diaphragm of the illumination system (illumination pupil of the excitation light 9) and image of the diaphragm of the detection system (detection pupil of the fluorescence signals 7) can for example also be masked per channel by a common, circumscribed rectangle. This reduces the demand on the manufacturing accuracy and does not significantly impair the channel cross-talk.

Thus, in such an embodiment the objective array 18 has a diaphragm array 23 which forms a mask for the illumination pupils of the excitation light 9 and the detection pupils of the fluorescence signals 7. In this case the diaphragm array 23 is located between the field lens array 19 and the pupil lens array 21 in the embodiment example shown. The diaphragm array 23 could, however, also be located between the pupil lens array 21 and the arrangement of a plurality of individual detection sites 2 (heating cover 16) and in this case for example near to the pupil lens array 21.

Figure 12:
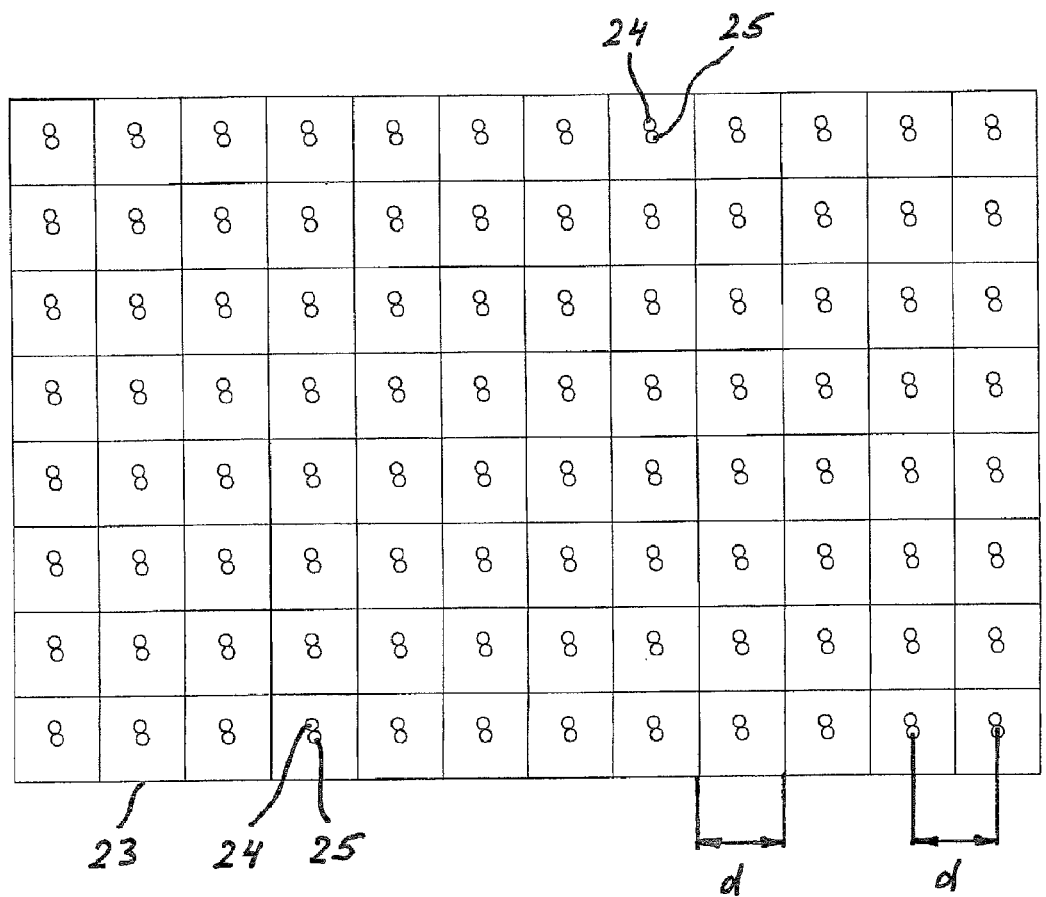
FIG. 12 shows a diaphragm array for masking the diaphragm images of the objective array.

FIG. 12 shows an example of a top-view of such a diaphragm array 23 in which each diaphragm array element is formed from a pair of diaphragm openings 24, 25. The diaphragm array 23 that is shown is thus provided with 96 pairs of diaphragm openings 24, 25 each of which are allocated to one of the 96 detection sites 2. The diaphragm opening pairs are arranged such that in each case a first diaphragm opening 24 of a diaphragm opening pair allows the excitation light 9 for a detection site 2 to pass through and a second diaphragm opening 25 of the diaphragm opening pair allows the fluorescence signals 7 from the detection site 2 to pass through. The course of the imaginary lines which delimit the squares elucidated above with an edge length corresponding to the hole spacing d and an area $A_Q$ is also shown for illustration. In real diaphragm arrays 23 these lines are usually not present.

The main function of the diaphragm array 23 is to suppress cross-talk between the various channels of the objective array 18. The cross-talk can be caused by internal reflections (directed interfering light) or undirected diffused scattered light in the objective array 18 and especially in the pupil lens array 21. The total area of the holes 24, 25 in the diaphragm array 23 is apparently very much smaller than the total area of the diaphragm array 23. This results in a very effective separation of useful light and interfering light which is indeed already very near to the site at which the fluorescence signals 7 are formed i.e. the detection sites 2 and thus at an early point in the detection beam path which is very advantageous for the optical detection. The ratio of these areas can in turn be interpreted as a filling factor. The effectiveness of the diaphragm array 23 with regard to suppressing cross-talk increases with a decreasing filling factor.

Certain features of the invention and further developments can be briefly summarized as follows: The objective array 18 comprises a field lens array 19 and a pupil lens array 21 as well as in certain embodiments can comprise an additional diaphragm array 23. The field lens array 19 generates illumination pupils and detection pupils in each case corresponding to the number of detection sites 2 (in the example 96 of each). The diaphragm array 23 masks these pupils (in the example 192) to prevent local cross-talk. The pupil lens array 21 forms an image of the field lens array 19 on the detection sites 2 (the multiwell plate). With regard to illumination the objective array 18 increases the filling factor (packing density) of the detection sites 2 (wells). With regard to detection the objective array 18 increases the numerical aperture. The geometry results in a nominal signal gain (here by a factor of 9).

Figure 13:
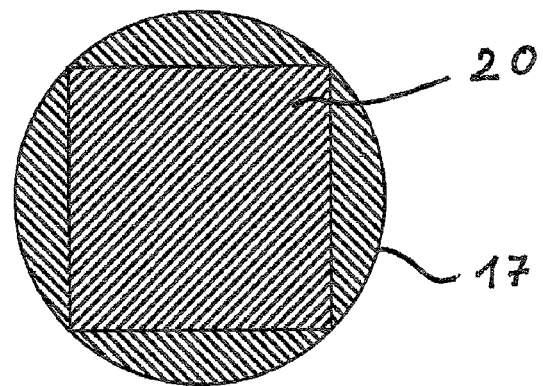
FIG. 13 shows a picture of a quadratic field lens array element in a circular hole of the heating cover.

The field lens array elements 20 of the field lens array 19 do not necessarily have to be designed with a round border. In an embodiment the field lens array elements 20 are quadratic. FIG. 13 shows an image of a quadratic field lens array element 20 in a circular hole 17 of the heating cover 16. With a quadratic border with an edge length which corresponds to the hole spacing d in the heating cover 16 (in this case 9 mm) one can join all field lens array elements 20 to one another without gaps i.e. without interspaces between the field lens array elements 20 that are unused for the optical imaging. If one now selects the imaging scale $\beta_Q$ as shown in FIG. 13 such that the four corners of the field lens array elements 20 are now imaged on the circular lower edges of the holes 17 of the heating cover 16 i.e. on the circular edges of the plurality of detection sites 2, then the proportion $\eta'_{AQ}$ of the utilized excitation light 9 is given by:

$$\eta'_{AQ} = 100\%$$

Apparently there is no shadowing neither on the field lens array 19 nor on the diaphragm array 23 nor on the heating cover 16.

The gain factor $g_{AQ}$ of the objective array 18 with quadratic field lens array elements 20 for fluorescence excitation is the ratio of $\eta'_{AQ}$ to $\eta_A$.

$$g_{AQ} = \frac{\eta'_{AQ}}{\eta_A} = 3.82 > g_A$$

The imaging scale $\beta_Q$ is given by the ratio of the diagonals ($\sqrt{2}\cdot d$) of the quadratic field lens array element 20 to the diameter D of the holes 17 in the heating cover 16:

$$\beta_Q = \frac{\sqrt{2}\cdot d}{D} = 2.45$$

In the case of quadratic field lens array elements 20 the numerical aperture $NA'_Q$ at the site of the heating cover 16 is:

$$NA'_Q = \beta_Q \cdot NA = 0.034$$

The solid angle $\Omega'_{DQ}$ detected by the detection optics with the aid of the objective array 18 is in this case:

$$\Omega'_D = 2\pi \cdot (1-\sqrt{1-NA'^2_Q}) = 4.0 \cdot 10^{-3}$$

The proportion $\eta'_{DQ}$ of the fluorescence light utilized by the objective array 18 is thus:

$$\eta'_D = \frac{\Omega_{DQ}}{\Omega_{tot}} = 2.9 \cdot 10^{-4}$$

The gain factor $g_{DQ}$ for fluorescence detection using the objective array 18 is, in contrast to the case of the round field lens array elements, no longer merely given by the ratio of $\eta'_{DQ}$ to $\eta_D$. Rather one must take into consideration that the entire circular area of the hole 17 is not imaged on the optical sensor 6 but rather only the circumscribed square. The quadratic field lens array element 20 acts as a corresponding field diaphragm. Thus:

$$g_{DQ} = \frac{\eta'_{DQ}}{\eta_D} \cdot \frac{2}{\pi} = 3.82$$

The total gain factor $g_{totQ}$ of the objective array 18 is the product of the gain factors for fluorescence excitation $g_{AQ}$ and fluorescence detection $g_{QD}$:

$$g_{tot,Q} = g_{AQ} \cdot g_{DQ} = 14.6$$

This value is considerably larger than the total gain factor $g_{tot}$ for round field lens array elements 20 of 9.0 (see above). As already mentioned the lower circular edges of the holes 17 of the heating cover 16 act as an array of field diaphragms when the objective array 18 is designed such that they are imaged in a true to shape manner on the edges of round field lens array elements 20.

Hence, in the case of quadratic field lens array elements 20, the field diaphragm effect of the heating cover 16 does not apply. This is synonymous with the fact that the light that emanates between the circle and square in FIG. 13 impinges on four neighboring field lens array elements 20. These field lens array elements 20 cannot, however, transfer this light onto the optical sensor 6. From the viewpoint of neighboring channels this light originates from the wrong aperture diaphragm in the objective array 18 which is a long way out of centre relative to the aperture diaphragm of the neighboring channel. Thus, rays which impinge on neighboring field lens array elements 20 have such large aperture angles that they cannot be directly detected by the detection optics.

This fluorescence light that cannot be detected directly can at most strike the optical sensor 6 as a result of multiple reflections or by scattering in the detection optics. This part of the signal would in principle be detrimental because it would with a very high probability be allocated to a false channel. However, in practical evaluations and using computationally intensive, non-sequential ray tracing, it was shown that this portion of scattered light, when quantified, is practically insignificant and negligible.

The imaging of the edges of the field lens array elements 20 on the border of the hole 17 in the heating cover 16 is a borderline case with regard to the gain factor. The four corners of the field lens array elements 20 are imaged on or within the circular lower edges of the holes 17 of the heating cover 16 i.e. on the circular edges of the plurality of detection sites 2. If the imaging scale $\beta_Q$ is selected:

$$\beta_Q > \sqrt{2}\cdot d/D = 2.45$$

the total gain factor $g_{tot,Q}$ is constant. The utilizable area of the square decreases but the associated loss is exactly compensated by the increasing numerical aperture. Conversely, the gain factor decreases because, on the one hand, the numerical aperture decreases but the area of the square does not increase in a corresponding manner. The latter is then clipped by the hole 17 in the heating cover 16.

Figure 14:
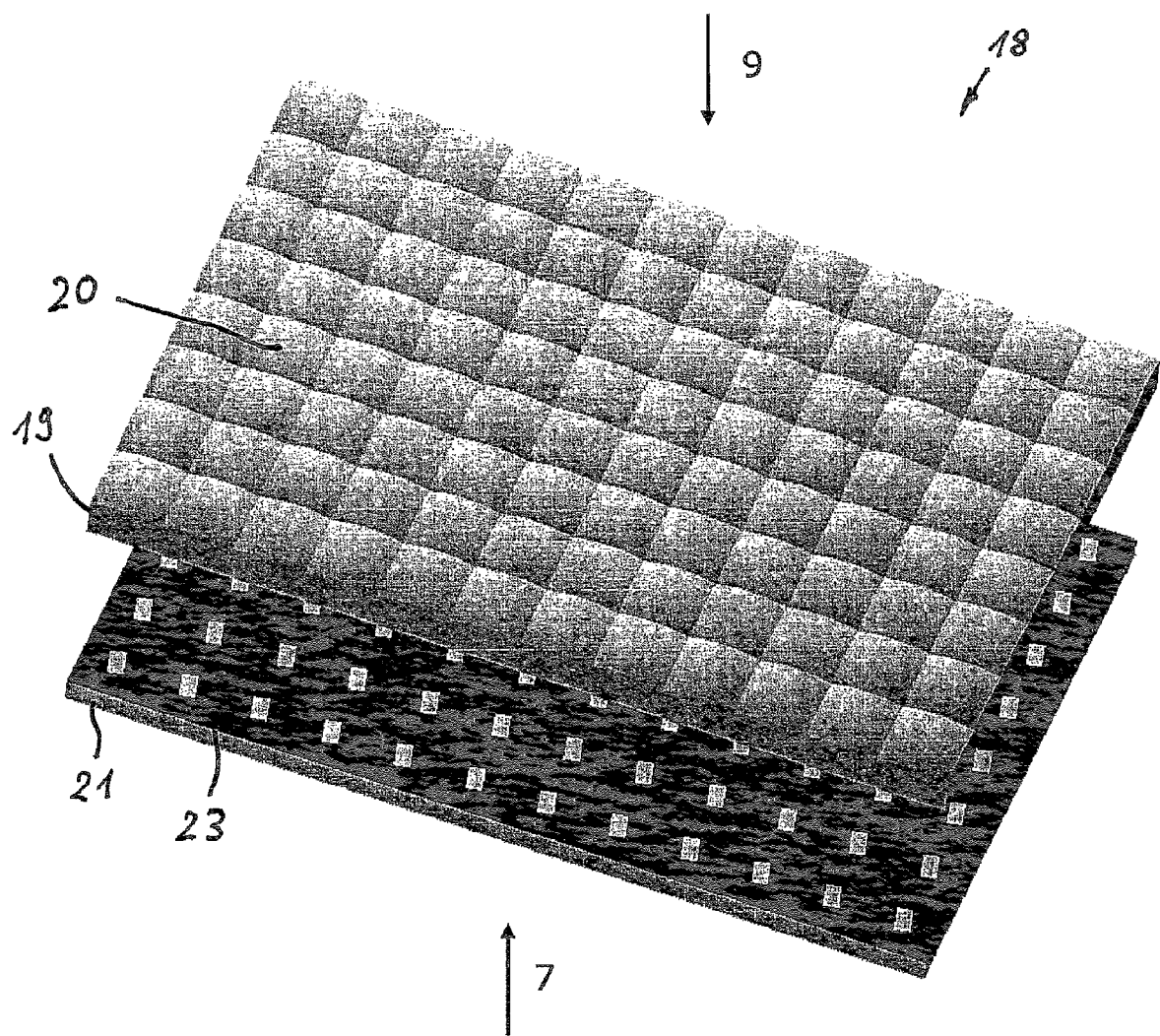
FIG. 14 shows an objective array with quadratically bordered field lens array elements in a view from above.
Figure 15:
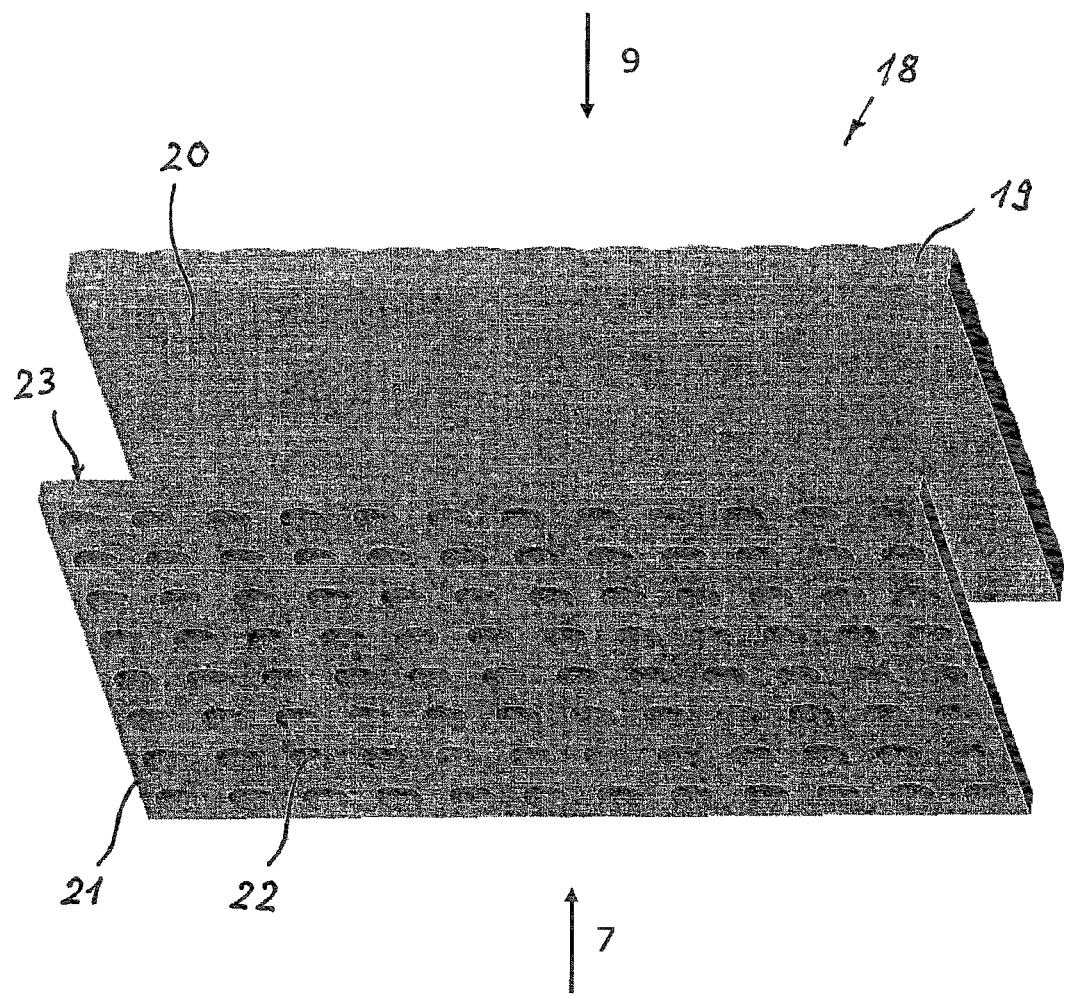
FIG. 15 shows the objective array of FIG. 14 in a view from below.

FIG. 14 shows such an objective array 18 with field lens array elements 20 having a quadratic border in a view from "above" i.e. from the side of the excitation light 9, and FIG. 15 shows the objective array 18 of FIG. 14 in a view from "below" i.e. from the side of the fluorescence signals 7. The diaphragm array elements (diaphragm openings in the diaphragm array 23) are in this case designed such that they have a rectangular shape and in each case only one diaphragm opening is present per channel of the field lens array 22 i.e. per field lens array element 20 and associated pupil lens array element 22 i.e. there is one common diaphragm opening for both the excitation light 9 and fluorescence signals 7 of the channel.

An optical instrument 1 according to the invention can be further complemented with features that are not referred to in this application according to the prior art and in particular according to EP 1 681 555 B1 or EP 1 681 556 B1, the disclosed contents of which are explicitly incorporated. In particular the following advantageous features can be realized in certain embodiments:

a) The field lens 8 is arranged such that it generates excitation light 9 having an angle of incidence α to the planar support 4 of the arrangement of a plurality of individual detection sites 2 which is larger than 0°. Expressed more precisely α is the angle between the axes of the illumination and detection system. One of the two axes is bent by the mirror or beam splitter 14.

b) The optical instrument 1 comprises a mirror or beam splitter 14 which is transparent for at least one excitation frequency and reflective for the frequencies of the fluorescence signals 7 or a beam splitter 14 which is reflective for at least one excitation frequency and transparent for the frequencies of the fluorescence signals 7.

c) The angle of incidence a of the excitation light 9 is less than 20°, for example less than 10° or less than 5°.

d) The angle of incidence α is $$\alpha \geq \theta_1 + \theta_2$$

in which $\theta_1$ is the aperture half-angle of the excitation optics and $\theta_2$ is the aperture half-angle of the imaging optics.

e) The imaging lens arrangement 11 is coupled to the optical sensor and forms an imaging unit 15.

f) The optical instrument 1 comprises a light beam folding unit comprising one, two or more folding mirrors wherein the folding unit is arranged such that it folds light from the light source 5 and fluorescence signals 7 from the arrangement of a plurality of individual detection sites 2.

g) The individual detection sites 2 of the arrangement represent wells, the excitation light 9 is parallel to the sidewalls of the wells and the solution which fills the wells contains fluorescent dyes.

h) The individual detection sites 2 of the arrangement represent wells, the excitation light 9 has an angle of less than 20° relative to the sidewalls of the wells and the solution which fills the wells contains fluorescent dyes.

i) The individual detection sites 2 of the arrangement are sites on a planar support 4 and fluorescent dyes are applied to these sites.

While the foregoing invention has been described in some detail for purposes of clarity and understanding, it will be clear to one skilled in the art from a reading of this disclosure that various changes in form and detail may be made without departing from the true scope of the invention. For example, the systems and methods described above may be used in various combinations. All publications cited in this application are incorporated by reference in their entirety for all purposes to the same extent as if each individual publications were individually indicated to be incorporated by reference for all purposes.

LIST OF REFERENCE NUMERALS 1 optical instrument
2 detection sites
3 holding device
4 planar support
5 light source
6 optical sensor
7 fluorescence signals
8 field lens
9 excitation light
10 excitation lens arrangement
11 imaging lens arrangement
12 excitation filter system
13 imaging filter system
14 beam splitter
15 imaging unit
16 heating cover
17 hole
18 objective array
19 field lens array
20 field lens array element
21 pupil lens array
22 pupil lens array element
23 diaphragm array
24 first diaphragm opening in 23
25 second diaphragm opening in 23
26 hole image
27 axial curve
28 outer axial curve
29 envelope
α angle of incidence
θ aperture angle
$A_L$ area of the hole (object)
$A_{LB}$ area of the hole (image)
$A_Q$ area of the square
d distance between the holes
D hole diameter
h ray height
NA numerical aperture

The invention claimed is:

1. An optical instrument for imaging fluorescence signals from an arrangement of a plurality of individual detection sites comprising:
   a holding device for holding a planar support with an arrangement of a plurality of individual detection sites;
   at least one light source for emitting light comprising at least one excitation frequency;
   an optical sensor for receiving fluorescence signals from the arrangement of a plurality of individual detection sites and capable of generating computer-readable primary data;
   a field lens for transferring the excitation light from the light source to the arrangement of a plurality of individual detection sites and transferring fluorescence signals from the arrangement of a plurality of individual detection sites to the optical sensor;
   an excitation lens arrangement for transferring excitation light from the light source to the field lens; and
   and imaging lens arrangement for transferring fluorescence signals from the field lens to the optical sensor;
   wherein:
      the optical instrument comprises an objective array comprising a field lens array having field lens array elements and a pupil lens array comprising pupil lens array elements, wherein the objective array is located in the light beam path between the field lens and the arrangement of a plurality of individual detection sites,
   and wherein:
      a diaphragm array forms a mask for illumination pupils from the excitation light and detection pupils from the fluorescence signals, wherein the diaphragm array has diaphragm array elements, each of said diaphragm array element comprising one or more diaphragm openings and each of said diaphragm array element being allocated one field lens array element and one pupil lens array element and forming a mask for the beam path through the respective field lens array element and pupil lens array element.

2. The optical instrument according to claim 1, wherein the objective array in each case a pair of lenses formed from a field lens array element and a pupil lens array element is in each case allocated to one of the detection sites.

3. The optical instrument according to claim 1, wherein the pupil lens array forms an image of the field lens array on the plurality of detection sites.

4. The optical instrument according to claim 1, wherein the field lens array generates illumination pupils for the excitation light and detection pupils for the fluorescence signals.

5. The optical instrument according to claim 1, wherein the plurality of detection sites have a diameter (D) and are arranged at a distance (d) to one another, and that the imaging scale (β) of the pupil lens array elements is equal to the ratio of the distance (d) to diameter (D).

6. The optical instrument according to claim 1, wherein the diaphragm array is arranged between the field lens array and the pupil lens array or between the pupil lens array and the arrangement of plurality of detection sites.

7. The optical instrument according to claim 6, wherein the diaphragm array is provided with pairs of diaphragm openings which are each allocated to one of the detection sites wherein the pairs of diaphragm openings are arranged such that in each case a first diaphragm opening of a pair of diaphragm openings allows the excitation light for a detection site to pass through and a second diaphragm opening of the pair of diaphragm openings allows the fluorescence signals from the detection site to pass through.

8. The optical instrument according to claim 1, wherein the beam path of the excitation light and the beam path of the fluorescence signals from the plurality of individual detection sites are telecentric on the object side of the field lens between the field lens and the field lens array.

9. The optical instrument according to claim 1, wherein the shape of the field lens array elements is selected from the group consisting of round and square.

10. The optical instrument according to claim 9, wherein the field lens array elements are square, the plurality of detection sites have a diameter (D) and are arranged at a distance (d) to one another, the four edges of the field lens array elements are imaged on or within the circular borders of the plurality of individual detection sites and that the imaging scale ($\beta_Q$) of the pupil lens array elements is the same as or more than the ratio of the diagonals ($\sqrt{2} \cdot d$) of the square field lens array elements to the diameter (D).

11. The optical instrument according to claim 1, wherein the light source is an LED.

12. An optical instrument for imaging chemiluminescence or bioluminescence signals from an arrangement of a plurality of individual detection sites comprising:
a holding device for holding a planar support with an arrangement of a plurality of individual detection sites;
an optical sensor for receiving chemiluminescence or bioluminescence signals from the arrangement of a plurality of individual detection sites and which is capable of generating computer-readable primary data;
a field lens for transferring chemiluminescence or bioluminescence signals from the arrangement of a plurality of individual detection sites to the optical sensor;
an imaging lens arrangement for transferring chemiluminescence or bioluminescence signals from the field lens to the optical sensor;
wherein
the optical instrument has an objective array comprising a field lens array with field lens array elements and a pupil lens array with pupil lens array elements, and wherein the objective array is arranged in the light beam path between the field lens and the arrangement of a plurality of individual detection sites.

13. A real-time PCR instrument comprising:
an optical instrument according to claim 1,
means for heating and cooling a support with one or more wells each containing a reaction mixture capable of performing a PCR reaction.

14. An analytical system for simultaneously performing and monitoring a plurality of PCR reactions in real-time comprising:
a multiwell plate as an arrangement of a plurality of individual detection sites each containing a reaction mixture capable of performing a PCR reaction,
fluorescent DNA binding entities capable of generating fluorescence signals and
a real-time PCR instrument according to claim 13 comprising an optical instrument according to claim 1 for illuminating the plurality of individual detection sites of the multiwell plate with light and for detecting the fluorescence signals from each well of the multiwell plate by an optical sensor which is arranged such that it can receive the corresponding fluorescence signals in order to generate computer-readable primary data.

15. A method for amplifying, detecting and/or quantifying a plurality of DNA target sequences comprising:
providing a composition or a reaction mixture which is able to carry out PCR reactions;
treating the reaction mixture according to a thermocycling protocol such that an amplification of the plurality of DNA target sequences can take place; and
determining the presence and the number of each DNA sequence at least once after a plurality of amplification cycles using fluorescent DNA binding entities and a real-time PCR instrument according to claim 13.

* * * * *